(12) United States Patent
Nozaki et al.

(10) Patent No.: US 10,138,450 B2
(45) Date of Patent: Nov. 27, 2018

(54) CELL CULTURE DEVICE

(71) Applicant: Hitachi, Ltd., Tokyo (JP)

(72) Inventors: Takayuki Nozaki, Tokyo (JP); Guangbin Zhou, Tokyo (JP); Masaharu Kiyama, Tokyo (JP); Ryota Nakajima, Tokyo (JP); Shizu Matsuoka, Tokyo (JP); Taku Nakamura, Tokyo (JP); Masakazu Sugaya, Tokyo (JP); Koichi Terada, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 527 days.

(21) Appl. No.: 14/768,770

(22) PCT Filed: Mar. 15, 2013

(86) PCT No.: PCT/JP2013/057510
§ 371 (c)(1),
(2) Date: Aug. 19, 2015

(87) PCT Pub. No.: WO2014/141477
PCT Pub. Date: Sep. 18, 2014

(65) Prior Publication Data
US 2016/0002584 A1    Jan. 7, 2016

(51) Int. Cl.
*C12M 1/00*    (2006.01)
*B01L 1/00*    (2006.01)
(Continued)

(52) U.S. Cl.
CPC ............ *C12M 21/08* (2013.01); *C12M 23/50* (2013.01); *C12M 23/58* (2013.01); *C12M 29/00* (2013.01); *C12M 41/14* (2013.01); *C12M 41/36* (2013.01)

(58) Field of Classification Search
CPC ...... C12M 23/50; C12M 33/04; C12M 29/10; C12M 23/04; C12M 23/40
See application file for complete search history.

(56) References Cited

U.S. PATENT DOCUMENTS 5,817,508 A * 10/1998 Berndt ................. B01L 3/5085
356/428
7,682,823 B1    3/2010 Runyon
(Continued)

FOREIGN PATENT DOCUMENTS

JP    2006-11415 A    1/2006
JP    2007-312668 A    12/2007
(Continued)

OTHER PUBLICATIONS

Extended European Search Report received in corresponding European Application No. 13877993.9 dated Oct. 4, 2016.
International Search Report of PCT/JP2013/057510.

*Primary Examiner* — Nathan A Bowers
(74) *Attorney, Agent, or Firm* — Mattingly & Malur, PC

(57) ABSTRACT

An automatic culture device which employs closed-system culture vessels and in which, when a passage part (2) and a rotational valve mechanism (3) are configured, the multiple culture vessels in a culture vessel part (1) can be rendered equal in liquid-feeding conditions by, for example, regulating the length of each passage. As a result, the evenness in quality of cells incubated in the multiple culture vessels is rendered possible. Furthermore, by providing a mechanism which enables a user to normally set passages in the device, the evenness in quality of the cells is rendered possible likewise.

16 Claims, 23 Drawing Sheets

(51) Int. Cl.
*C12M 3/00* (2006.01)
*C12M 1/34* (2006.01)

(56) References Cited

U.S. PATENT DOCUMENTS

| | | |
|---|---|---|
| 2005/0282268 A1 | 12/2005 | Kagayama |
| 2009/0137026 A1 | 5/2009 | Kobayashi et al. |
| 2010/0151564 A1* | 6/2010 | Beebe .................. C12M 23/10 435/288.7 |
| 2014/0106386 A1* | 4/2014 | Umeno .............. G01N 35/0099 435/23 |

FOREIGN PATENT DOCUMENTS

| | | |
|---|---|---|
| JP | 2009-125027 A | 6/2009 |
| JP | 2009-251297 A | 10/2009 |
| JP | 2010-75200 A | 4/2010 |
| JP | 2012-039929 A | 3/2012 |

\* cited by examiner

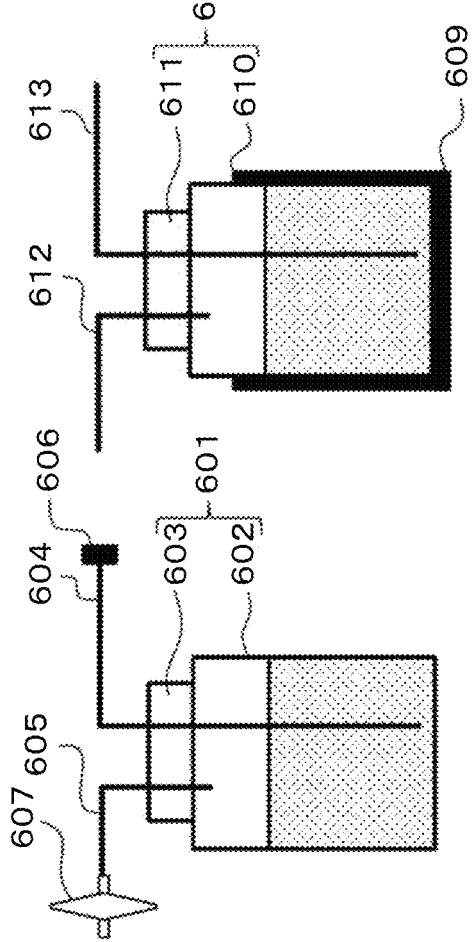

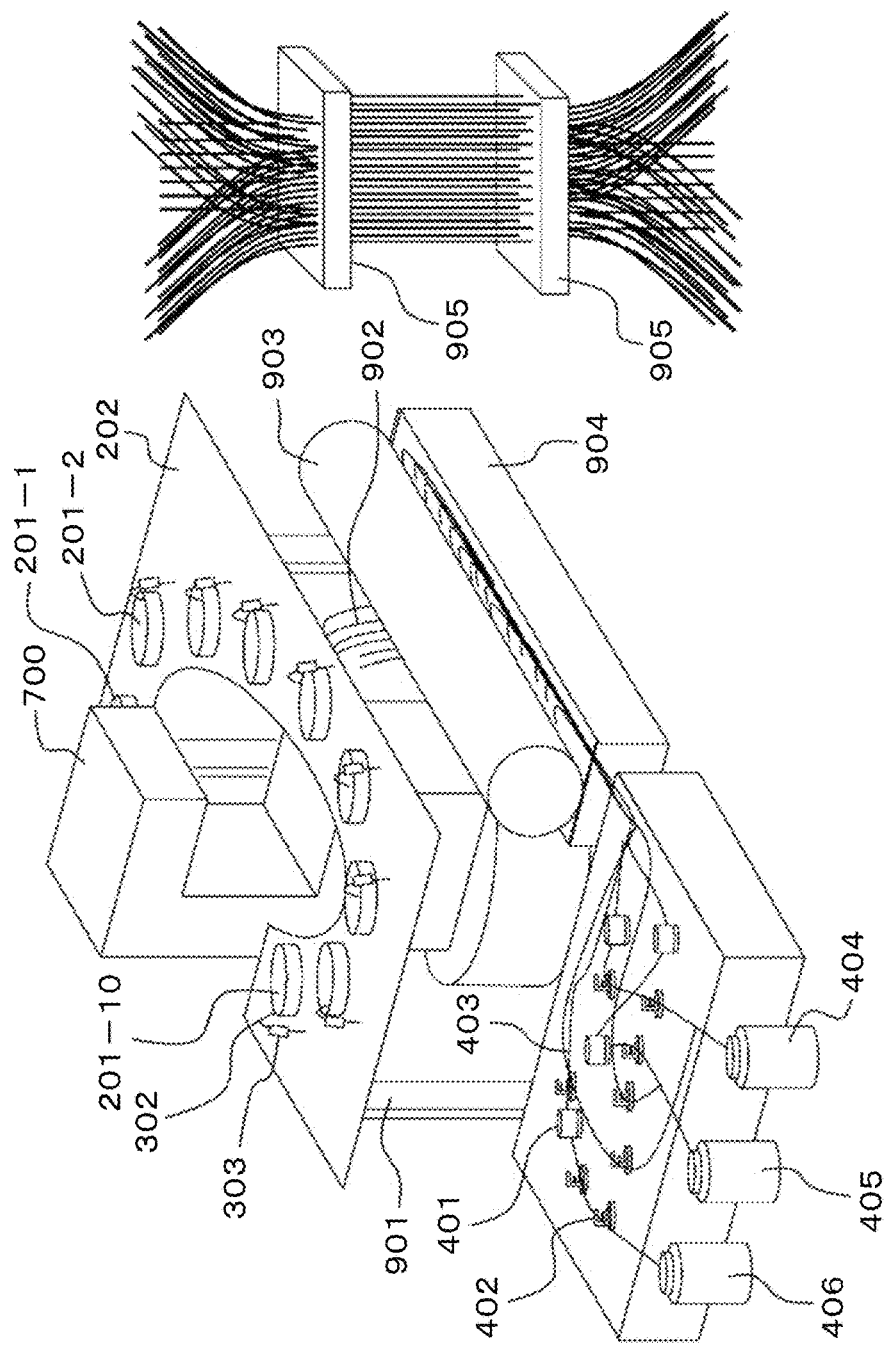

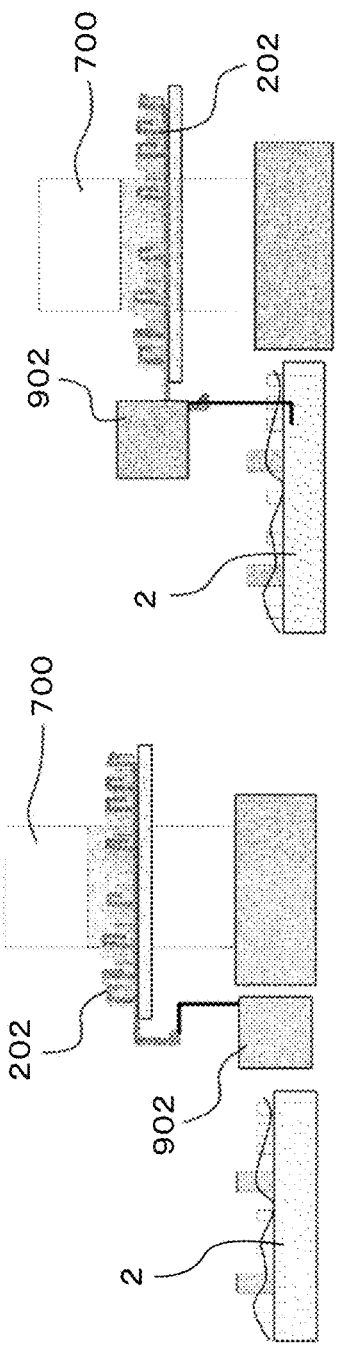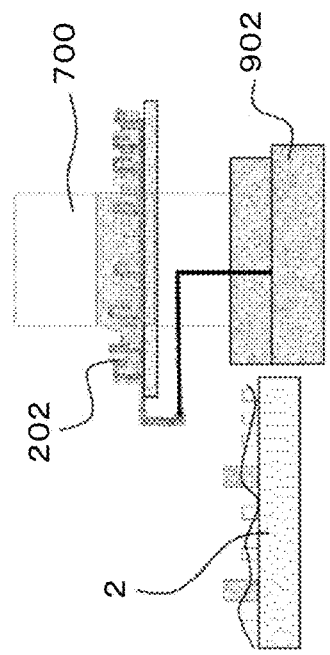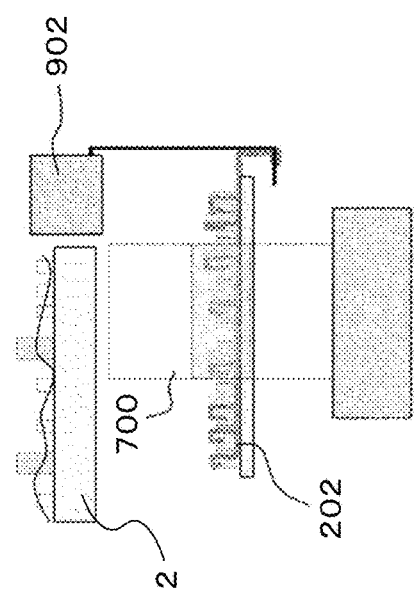

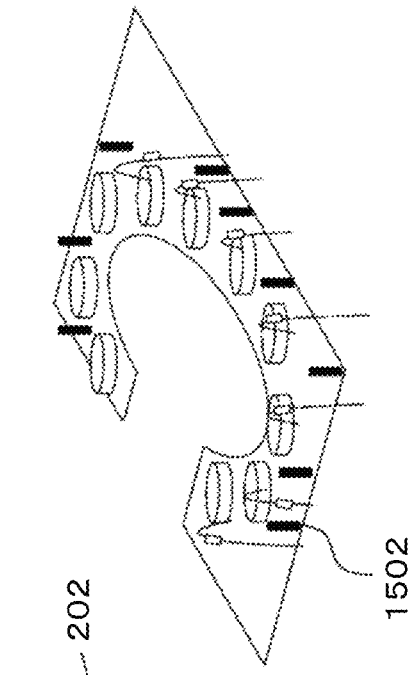
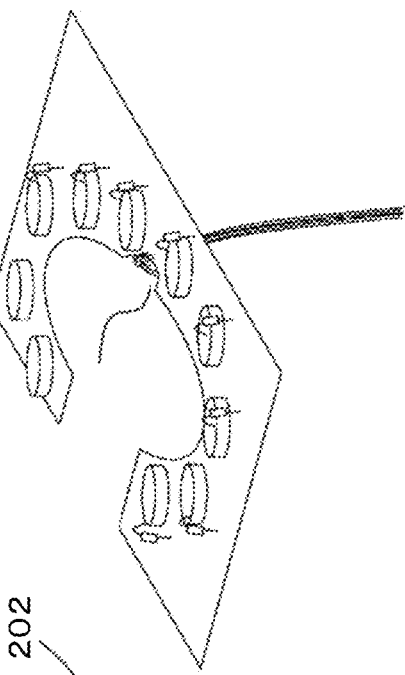
FIG. 15A
FIG. 15B
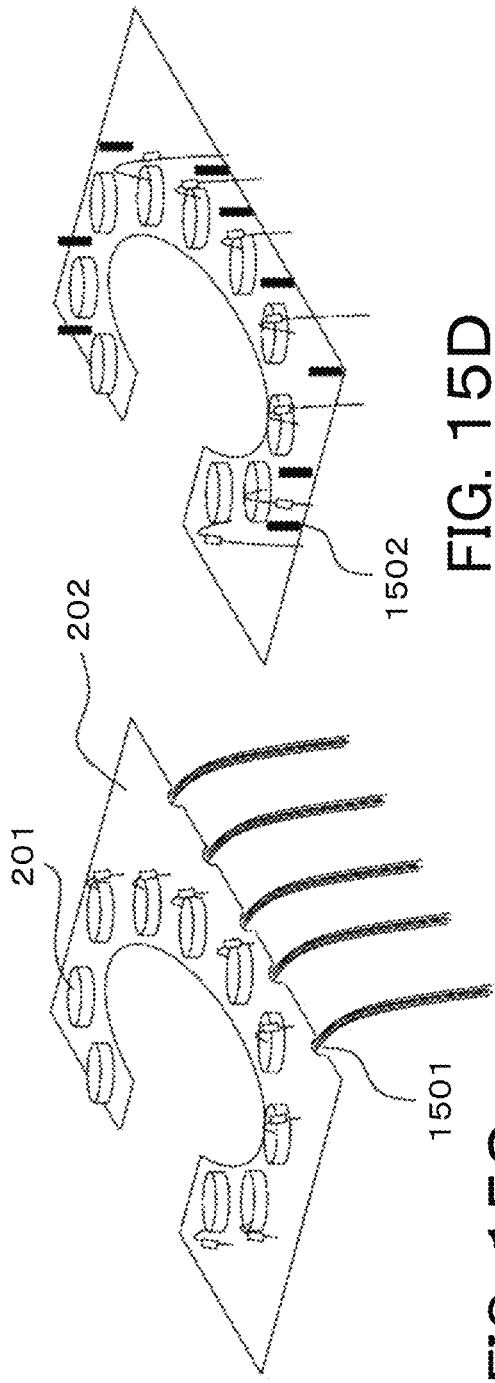
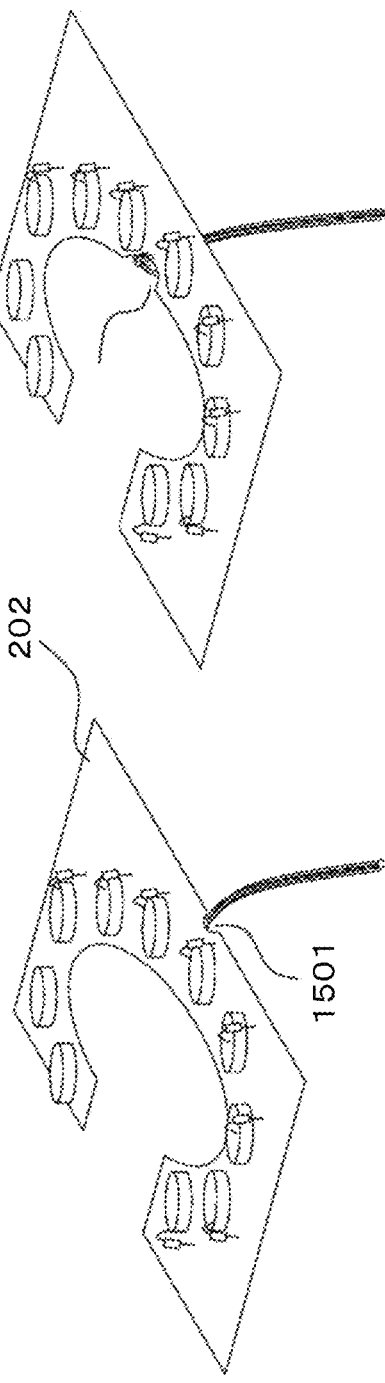
FIG. 15C
FIG. 15D

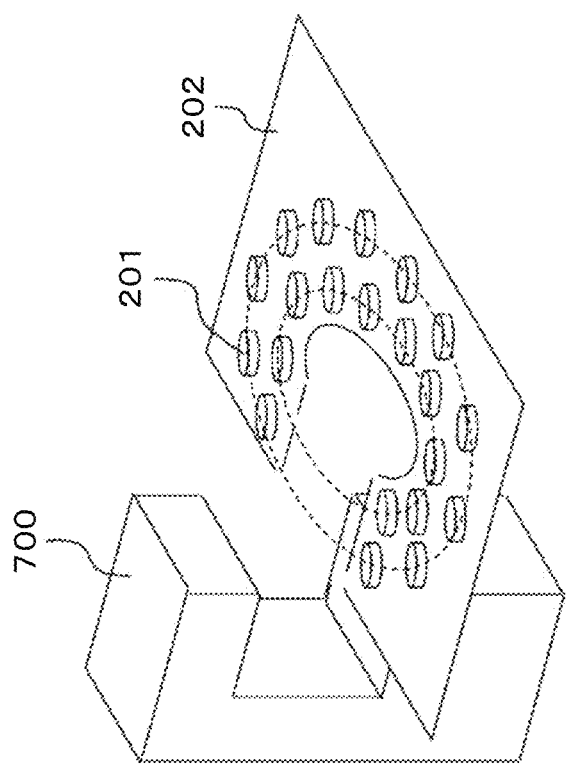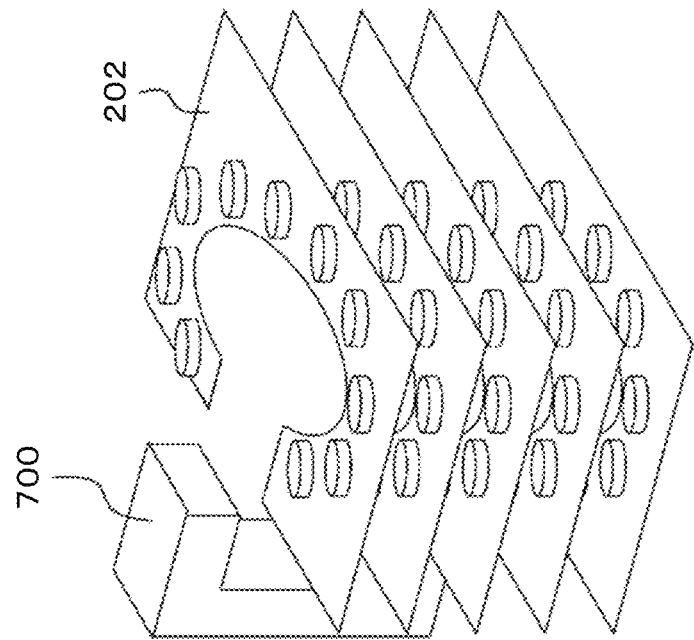

CELL CULTURE DEVICE

TECHNICAL FIELD

The present invention relates to a culture device that cultures cells or tissue by automatic manipulation.

BACKGROUND ART

Tissue engineering is expected as a treatment which is sure to effect a cure for diseases having no treatment methods conventionally in which the functions of organs and the like are recovered using biological samples such as regenerated tissue and the like manufactured using cells as raw materials. Regenerated tissue is manufactured by manufacture practitioners specialized in cell culture techniques at a CPC (Cell Processing Center) providing a clean manufacture environment in accordance with the SOP (Standard Operating Procedure). Thus, enormous personnel costs, man-power, and operation costs occur. Moreover, since all the manufacturing processes are performed by hands, a limit is imposed on the amount of manufacture of regenerated tissue. On this account, manufacturing costs are increased, and hamper the spread of tissue engineering and treatment as a consequence.

In order to move beyond the status quo, it is desired to introduce an automatic culture device that automates a part or all of cultivation processes. This makes possible to perform the cultivation processes using an automatic culture device without hands and to realize labor saving, cost reduction, and mass production. In addition, it is also expected to provide the contribution to the constant quality of regenerated tissue because the manipulations of the automatic culture device are constant.

Here, the automatic culture device is a replacement of manual operations, and it is necessary to comply with the GMP (Good Manufacturing Practice) for manual operations. Moreover, the GMP specialized for automatic culture devices is not presently defined. However, the Ministry of Economy, Trade and Industry presents the guidelines on the development of automatic culture devices for clinical applications (the fields of tissue engineering (the guidelines on the design of human cell culture system, revision (2009)), and it is also necessary to comply with the guidelines. From the description above, in consideration of the GMP for manual operations and the guidelines on the development of automatic culture devices, the automatic culture device is demanded that the automatic culture device be enabled to manufacture regenerated tissue of high quality in an excellent reproducibility in the state in which a clean environment is maintained based on scientific grounds.

For a scheme to solve the problems, Patent Literature 1, for example, discloses a device in which the lengths of passage tubes from a solenoid valve are aligned in units of columns for a plurality of culture vessels disposed in a matrix Configuration, cells are cultured using a plurality of the culture vessels in the same column matrix, and the quality of regenerated tissue is made equal.

Moreover, Patent Literature 2 discloses a device in which in order to decrease biological contamination risks, components including culture vessels, culture medium bottles, and the like necessary for cultivation are in connection all the time using passage tubes and the like and a closed-system cultivation space is formed.

CITATION LIST

Patent Literature

Patent Literature 1: Japanese Unexamined Patent Application Publication No. 2010-75200
Patent Literature 2: Japanese Unexamined Patent Application Publication No. 2007-312668

SUMMARY OF INVENTION

Technical Problem

However, in the adjusting method for the length of the passage described in Patent Literature 1, since only the lengths of the passages for the culture vessels disposed on the same column are aligned, there is a problem in that the degree of a loss of cells is varied for individual culture vessels in units of columns when a cell suspension for use in cultivation is delivered and it is not enabled to uniformize quality among a plurality of culture vessels cultured at the same time.

Moreover, the automatic culture device described in Patent Literature 2 has a problem in that in the passage setting operation on the device by a user, the user makes an operation error such as a collision to another equipment when a culture vessel is loaded into and unloaded out of the device and it is likely that this error causes the degradation of the quality of cultured cells.

The present invention is made in consideration of these problems, and there is provided a closed-system cell culture device that allows cell cultivation of high quality and excellent reproducibility. More specifically, there is provided a cell culture device that can uniformize the quality of cells after manufactured and can suppress operation errors by a user when passages are disposed, for example.

Solution to Problem

In order to solve the problems, the present invention is to provide a cell culture device that cultures cells including: a liquid solution holding part that holds a liquid solution for use in cultivation; and a plurality of passages that individually connects the liquid solution holding part to a plurality of culture vessels. In the cell culture device, the plurality of the passages has a length equal from the liquid solution holding part to the plurality of the culture vessels.

Moreover, in order to solve the problems, the present invention is to provide a cell culture device that cultures cells including: a liquid solution holding part that holds a liquid solution for use in cultivation; a plurality of culture vessels that holds the liquid solution supplied from the liquid solution holding part; a multi-branch part connected to the liquid solution holding part, the multi-branch part passing the liquid solution; and a plurality of passages that individually connects the multi-branch part to the plurality of the culture vessels and supplies a liquid solution passed through the multi-branch part to the plurality of the culture vessels. In the cell culture device, the plurality of the passages has a length equal from the multi-branch part to the plurality of the culture vessels.

Advantageous Effects of Invention

In accordance with the cell culture device using the closed-system culture vessel according to the present invention, it is possible to culture cells of high quality. More specifically, it is implemented to provide uniform cells of high quality cultured in a plurality of the culture vessels. Moreover, a mechanism that normally performs the passage setting operation to the device by the user suppresses the degradation of the quality of cells caused due to operating errors by the user.

BRIEF DESCRIPTION OF DRAWINGS

FIG. 6 is a diagram of examples of a cell bottle, a preheat bottle, and a humidification bottle included in the passage circuit according to the first embodiment.

FIG. 9 is a diagram of examples of a passage part and a microscope of the automatic culture device according to the first embodiment.

FIG. 12 is a block diagram of an exemplary layout of the functional configuration of the automatic culture device according to the first embodiment.

FIG. 15 is a diagram of culture vessel bases according to the first embodiment and a second embodiment.

FIG. 19 is a diagram of culture vessel bases according to a sixth embodiment.

DESCRIPTION OF EMBODIMENTS

Figure 1:
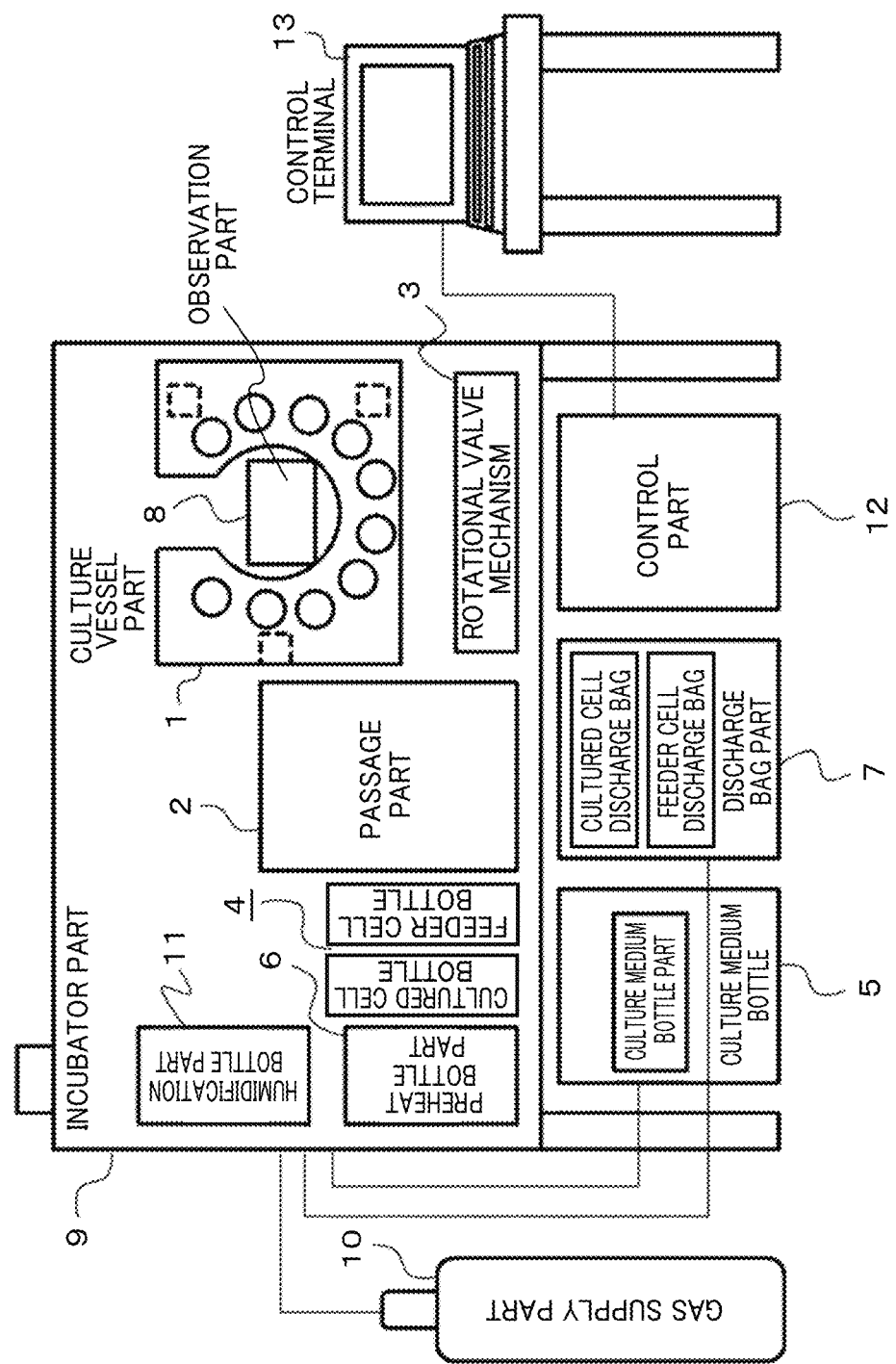
FIG. 1 is a diagram of the overall structure of an automatic culture device according to a first embodiment that cultures regenerated tissue.

In the present specification, a gas, a liquid, and a gas and a liquid flowing through the passages of the culture device are sometimes called a fluid for a general term. For the numbers denoted for components in the drawings, numbers on the drawings are sometimes omitted for components already numbered and described in other drawings. Moreover, diagrams of a culture vessel and passages are to be diagrams in the state in which a culture vessel is separated from a passage or separated from a part of a passage.

First Embodiment

First, basic configurations and operation flows of a cell culture device acceding to embodiments including a first embodiment will be described in detail with reference to the drawings. However, the basic configurations and operation flows are not limited to these ones, and it may be fine that configurations are appropriately added and operation flows are changed, for example, according to purposes.

In the following, for an example of the basic configuration of an automatic culture device, an automatic culture device formed of twelve components will be described in detail with reference to FIG. 1. In other words, twelve components include a culture vessel part 1, a passage part 2, a rotational valve mechanism 3, a cell bottle part 4 for cultured cells and feeder cells, a culture medium bottle part 5 configured of a refrigerator and the like, a preheat bottle part 6, a discharge bag part 7, an observation part 8, an incubator part 9, a gas supply part 10, a humidification bottle part 11, and a control part 12. It is noted that as illustrated in FIG. 1, the control part 12 includes a control terminal 13.

In the automatic culture device including the components described above, a cell suspension and a culture medium in a cell bottle and a culture medium bottle disposed by a user are used in a closed-system passage that is a closed cultivation space, solenoid valves, tube pumps, and the like, not illustrated, provided on the passage part 2 and the like are controlled by the control part 12, and cells are seeded in the culture vessels of the culture vessel part 1 for cultivation.

Moreover, the observation part 8 including a microscope and the like equipped on the device is controlled by the control part 12 during cell cultivation, and a cell image in the culture vessel is taken. The microscope is manually observed to allow the control of the position of the microscope, and shooting and storing cell images based on the input from the manipulation screen of the control terminal other than in automatic shooting, cell seeding, culture medium replacement, and gas exchange.

In the inside of the incubator part 9 of the automatic culture device, a temperature environment is observed using a sensor mechanism, and the observed result is displayed on the control terminal 13. All of logs for the operations of the solenoid valves, the tube pumps, and the like of the passage part 2 and measurement are recorded on a storage part such as a hard disk, not illustrated, provided in the control terminal 13. In addition, the presence or absence of an operation error is determined, and the situations of the operation are displayed on the monitor screen of the control terminal 13. These items of data can be transferred to the outside of the automatic culture device.

Figure 2:
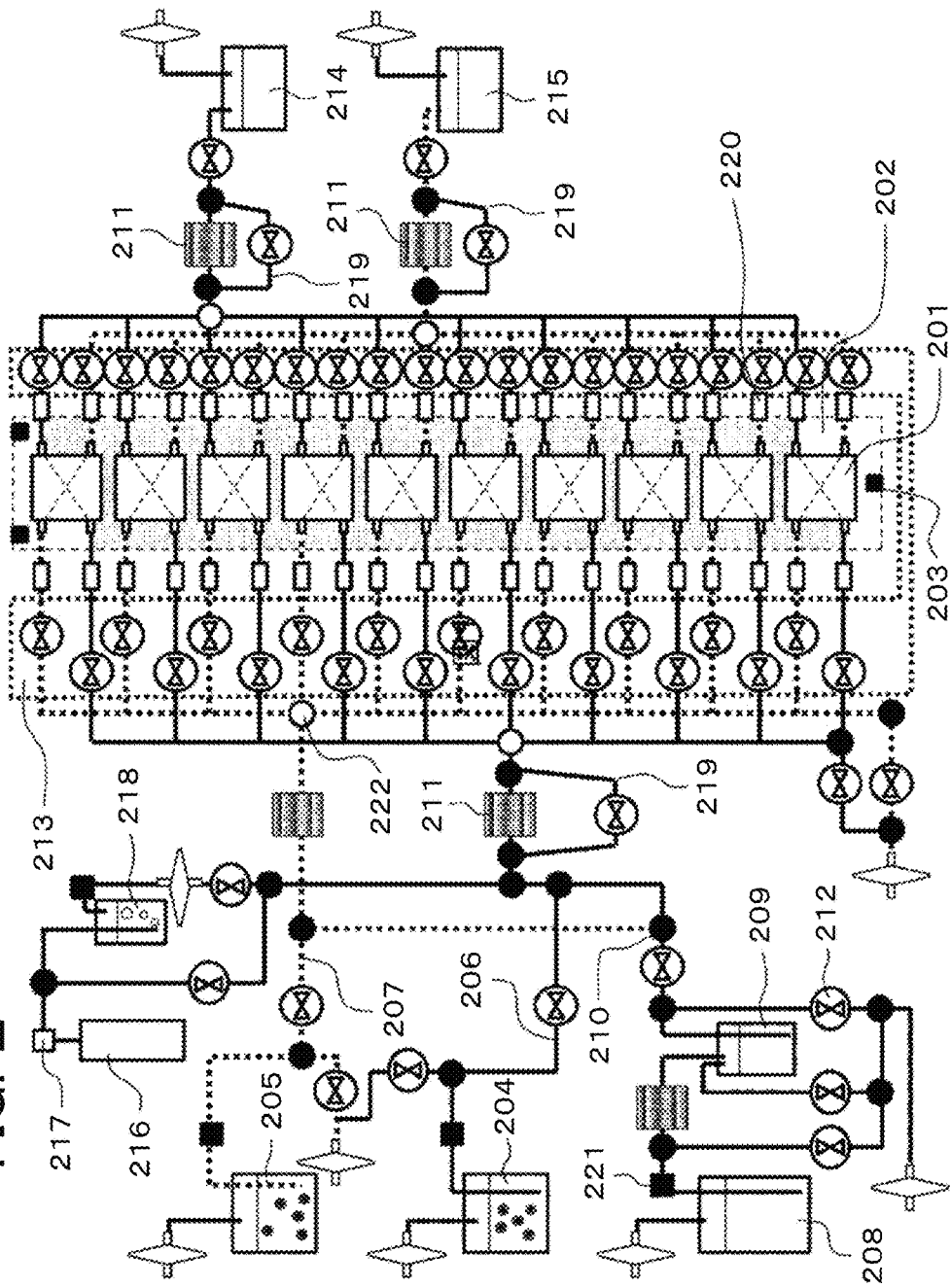
FIG. 2 is a diagram of a passage circuit of a closed-system passage of the automatic culture device according to the first embodiment.

FIG. 2 is a passage circuit of the closed-system passage of the automatic culture device described above. The closed-system passage includes the culture vessel part 1, the passage part 2, the rotational valve mechanism 3, the cell bottle part 4, the culture medium bottle part 5, the preheat bottle part 6, the discharge bag part 7, the gas supply part 10, and the humidification bottle part 11 in the components illustrated in FIG. 1.

In the first embodiment, the case is taken as an example for description in which the purpose is the manufacture of regenerated tissue for epithelial cells such as corneal epithelial cells, oral mucosal epithelial cells, and epidermal cells. However, the kinds of cells that can be cultured using the culture cell device are not limited to these cells. Moreover, in FIG. 2, the passage circuit uses two kinds of cells because targets are epithelial cells. However, in the case where a cultivation target is only one kind of cells such as cardiac muscle cells and fibroblasts, it may be fine that one cell bottle and the passage circuit of the passage for the cell bottle are provided. Alternatively, it may be fine that only a passage circuit targeted for one kind of cells is used in the passage circuit using two kinds of cells. Furthermore, the passage circuit in FIG. 2 uses ten culture vessels, and it is also possible that such a passage circuit is used in which the passage circuit includes a different number of culture vessels by disposing or removing the culture vessels in a parallel manner.

The closed-system passage illustrated in FIG. 2 mainly includes components below. In this example, ten culture vessels 201 are included in order to manufacture ten pieces of regenerated tissue. All the culture vessels 201 are disposed on a culture vessel base 202 in a flat plate, and an actuator 203 that changes the inclination is mounted on the culture vessel base 202.

As described above, two cell bottles 204 and 205 are used because two kinds of cells are used in this example. One kind of cells is put into the cell bottles 204 and 205. Moreover, in order to avoid mixing of two kinds of cells in the culture vessel, all the culture vessels have a two-layer structure, and one kind of cells is cultured on the individual layers. For the passage circuit from the cell bottles 204 and 205 to the layers of the culture vessels, different passage circuits (1) and (2) are used in order to prevent cells from being mixed in the midway point of liquid delivery. A cell suspension in the cell bottle 204 is passed through a passage circuit (1)206 depicted by a solid line, and delivered to the layers on one side of the culture vessels, the upper layers of all the culture vessels, for example. As described above, the passages are separated depending on cell species, so that it is suppressed to mix cells cultured on the upper layer of the culture vessel with cells cultured on the under layer, and it is possible to avoid the risks of the transplantation of different species, for example. On the other hand, a cell suspension in the cell bottle 205 is passed through a passage circuit (2)207 depicted by a dotted line, and delivered to the layers on one side of the culture vessels, the under layers of all the culture vessels, for example. It is noted that in FIG. 2, 222 denotes a multi-branch part, described later.

Although the cell bottles are differently provided for the individual cell species, the culture medium is used in common, and one culture medium bottle 208 is used. As described in FIG. 1, the culture medium bottle is stored at a temperature of 4° C. using refrigerator. When the culture medium is replaced, the amount necessary for one culture medium replacement is moved to a preheat bottle 209, heated to a temperature of 36° C., for example, and used for culture medium replacement. The passage is appropriately branched from the preheat bottle to the passage circuit (1)206 and to the passage circuit (2)207 through a two-branch part 210. The culture medium is delivered to the passage circuit (1)206, and then in turn delivered to the layers on one side of the culture vessels. The culture medium delivered to the passage circuit (2)207 is similarly delivered. The driving force for liquid delivery and air supply in the passage is provided from a tube pump 211. The direction of liquid delivery is controlled using a solenoid valve 212 and a rotational valve mechanism 213 corresponding to the rotational valve mechanism 3 in FIG. 1. When the culture medium is replaced, the old culture medium used for cultivation is delivered to discharge bags 214 and 215.

In cultivation, oxygen and carbon dioxide are supplied to the culture vessels 201 for gas exchange because cells consume oxygen and release carbon dioxide. In the device, when a gas is exchanged, the flow rate is adjusted at a predetermined gas supply rate using a gas cylinder 216 filled with air including 5% of $CO_2$ through a gas flowmeter 217, the air is passed through a humidification bottle 218 having sterilized water, and moisture is saturated to supply the air. The air is passed through a gas supply circuit 219 located in a parallel manner with the tube pump 211, and the air is delivered to the culture vessels.

For another configuration of the passage circuit according to the embodiment, a sterile detachable part 220 and a sterile connecting part 221 are included. The sterile detachable part 220 is disposed on the passage tubes near the culture vessels 201. With this configuration, in order to test one culture vessel as a sample on the day before transplantation, for example, a culture vessel can be removed in a sterile manner. The sterility of the removed culture vessel and the remaining culture vessels and the passages after removal can be maintained. On the day of transplantation, the culture vessel 201 is removed using the sterile detachable part 220 when the remaining culture vessels 201 are removed. The sterile detachable part 220 is a thermally weldable passage tube, for example, and a portion between two places including a cut place is cut after thermal welding.

On the other hand, the sterile connecting part 221 is disposed on the passage tubes near the cell bottles 204 and 205, the culture medium bottle 208, and the humidification bottle 218. The cell bottles 204 and 205, the culture medium bottle 208, and the humidification bottle 218 are loaded on a CPC (Cell Processing Center) in an empty state, a predetermined cell suspension, culture medium, and sterilized water are put into the bottles by the user, and the bottles are mounted on the closed-system passage. In the mounting, the sterile connecting part 221 is used in a sterile manner for connection.

Figure 3A:
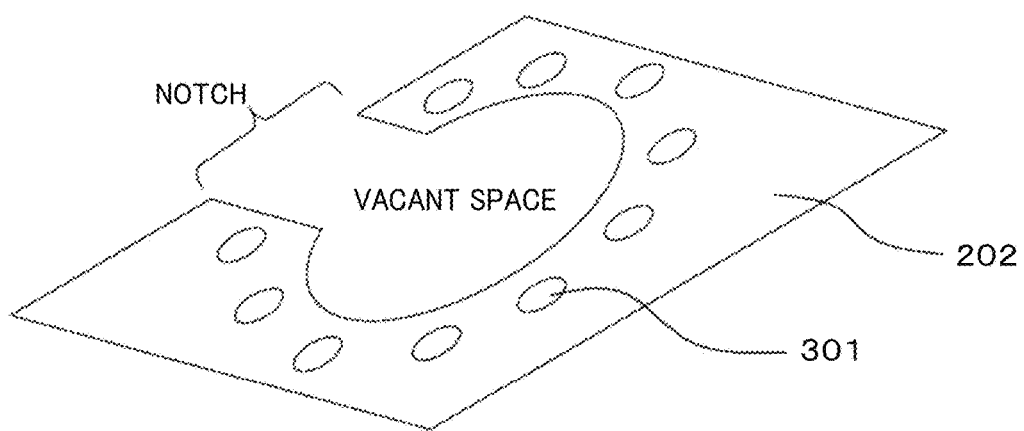
FIG. 3 is a diagram of an exemplary culture vessel base included in the passage circuit according to the first embodiment.
Figure 3B:
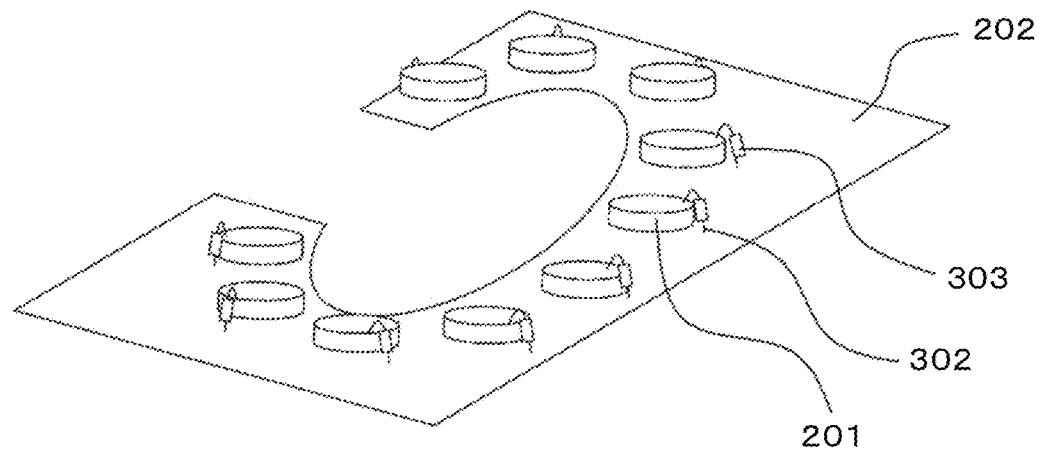

FIG. 3 is the culture vessel base 202 of the device according to the embodiment and an exemplary state of ten culture vessels 201 disposed on the culture vessel base 202. As illustrated in (A) on the upper part in FIG. 3, the culture vessel base 202 in this example has a horseshoe shape. In other words, the culture vessel base 202 has a so-called U shape in a structure in which the center part of a flat plate in a square shape is cut to form a vacant space and a notch is provided on the end on the side on which the culture vessel is inserted into the flat plate in the device, that is, the notch is provided on a part of the outer circumference. The inner edge of the center part of the culture vessel base 202 is in a circular shape, and the culture vessels 201 are disposed circularly around the edge. The culture vessel base 202 is formed with a holding part such as a recess for holding the culture vessel 201. The microscope of the observation part 8, described later, is disposed on the cut, circular vacant space portion. On the portion that holds the culture vessel 201, an observation hole 301 is provided for microscopic observation.

Since the culture vessel base 202 is in a U-shape as described above, the disposing direction on the device is uniquely determined. In other words, when the culture vessel base 202 is disposed, the culture vessel base 202 is brought close to the microscope from the notch side, the notch that is formed on one edge of the culture vessel base 202, the microscope is guided into the vacant space, and the culture vessel base 202 is disposed on the actuator or the like. With the shape having this cutout vacant space, the culture vessel base 202 can be disposed in the center of a plurality of the culture vessels 201. Moreover, the user can easily dispose and remove a plurality of the culture vessels 201 on the culture vessel base 202 as the culture vessels 201 are not contacted with the microscope, so that it is possible to suppress the degradation of the quality of cell cultivation caused by the damage of the passages and the like because of human errors.

Furthermore, it may be fine that another base for disposing the culture vessels is provided in the device, which the base in the same shape as the culture vessel base 202 and divided into a plurality of pieces, not illustrated, is provided, the culture vessel base 202 is placed on this another base for disposing the culture vessels, and disposing work is more facilitated even in the case where the weight of the culture vessel base is heavy, for example.

(B) on the lower part in FIG. 3 is a state in which ten culture vessels 201 are disposed on the culture vessel base 202. In the embodiment, four bundled passage tubes 302 are connected to the individual culture vessels 201, and these four passage tubes 302 are disposed in the outer direction with respect to the culture vessel base 202. The passage tubes 302 are disposed on the outer side of the culture vessel base 202, that is, on the outer circumference, so that it is possible to suppress the degradation of the quality of cells caused by contacting the microscope with the culture vessel base 202, the passage tube, and the like when the microscope is driven. A sterile detachable part 303 that can remove the individual culture vessels are included in the passage tubes near the culture vessels 201. Thus, for example, when only a given culture vessel is removed and evaluated in order to determine for shipment whether cells have quality that the cells can be subjected to transplantation on the day before transplantation, sterility is maintained in the inside of the removed culture vessel, the inside of the culture vessel not removed, and inside of the passage even after removal.

For example, in the case where a temperature response cell culture insert vessel produced by CellSeed Inc. is adapted, the cultivation surface of the culture vessel is changed in which when the temperature of the culture vessel 201 is decreased below the phase transition temperature of the temperature response cultivation surface, a temperature of 32° C., for example, the property of the temperature response cultivation surface is changed from the hydrophobic property to the hydrophilic property, cells adhered, extend, and reproduced in cultivation at a temperature of 37° C. are spontaneously peeled. When cells are peeled off from the temperature response cultivation surface caused by a temperature decrease, the cultivation conditions are greatly changed, and the quality of cells is also changed in transplantation. Therefore, in order not to greatly decrease the temperature of the culture vessels 201 remaining after removal on the previous day and the inside of the incubator part 9 below a temperature of 37° C., a flap for unloading on the days before the completion of cultivation is prepared on the upper part of the door of the incubator part 9 for the purpose of the confirmation of quality in the process of cultivation, and the effect is obtained that the time and area of the inside of the incubator part 9 to be exposed to the outside air are decreased and that the temperature in the operation is decreased. Moreover, the flap for unloading on the day before transplantation is formed of a transparent material such as glass, so that it is possible to confirm the progress of cultivation, including pH exhibited by the color of the culture medium and the presence or absence of biological contamination from the presence or absence of turbidity, for example, through the flap.

In unloading on the day of transplantation, after all the passage tubes connected to the culture vessels are cut in a sterile manner, a plurality of the culture vessels is removed from the device in the state in which the culture vessels are disposed on the culture vessel base, and the culture vessels are carried to a safe cabinet, for example, in the state in which the culture vessels are placed on the culture vessel base. In other words, a plurality of the culture vessels can be collectively handled. It is possible to avoid human errors such as one culture vessel left in the device. Moreover, such an advantage is also provided that the temporal conditions are the same as the temperature conditions for unloading the culture vessels.

Figure 4:
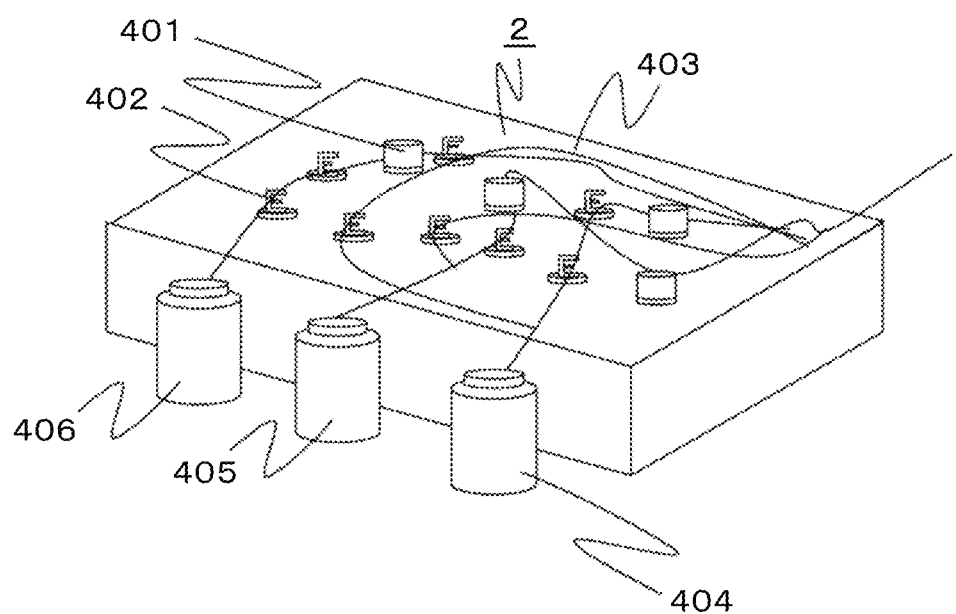
FIG. 4 is a diagram of an exemplary passage part included in the passage circuit according to the first embodiment.

As illustrated in FIG. 4, the passage part 2 is disposed with a tube pump 401, a solenoid valve 402, a passage tube 403, cell bottles 404 and 405, a preheat bottle 406, and the like. It is noted that in the embodiment and the other embodiments, a liquid solution holding part is sometimes referred as a general term for these bottles.

The tube pump 401 squeezes the passage tube 403 from the outside of the passage tube, and delivers a liquid or air. The solenoid valve 402 opens and closes the passage tube 403 by carrying a current, and controls the direction of liquid delivery or air supply. In disposing a filter, a filter having a hole diameter of 0.22 μm, for example, is used in order that the filter adjusts pressures in the inside and the outside of the passages and prevents germs and the like from being entered from the outside of the passages. In this case, for the disposition of the tube pump, the solenoid valve, the filter, and the branch part of the passage part 2, the positions are determined according to the conditions of the following priority.

The first condition is that the lengths of the passages from the cell bottle including the cell suspension of epithelial cells of the cell bottle part 4 to the culture vessels 201 are the shortest and equal length. The top priority is that the influence causing a trouble on the cultivation of epithelial cells, which are a cultivation target, in the seeding process is at the minimum.

The second condition is that the lengths of the passages from the cell bottle including a cell suspension of feeder cells of the cell bottle part 4 to the culture vessels 201 are the shortest and equal length. It is also desirable to minimize the influence causing a trouble on the cultivation of feeder cells that calculates a growth factor given to epithelial cells in the seeding process is at the minimum.

The third condition is that the lengths of the passages from the culture medium bottle including the culture medium of the culture medium bottle part 5 to the culture vessels 201 are the shortest and equal length. The condition is provided to avoid a decrease in the accuracy of the amount of liquid delivery caused by the attachment of protein and the like, which is a culture medium component, to the inside of the passage tube, and the remaining droplet by delivering the culture medium through the shortest passage route.

In the device according to the embodiment, as for the point that the lengths of the passages to the culture vessels 201 are made equal in the first to third conditions, since the length from the liquid solution holding part to the multi-branch part 222 is common in the culture vessels, the lengths from the multi-branch part 222 to the culture vessels 201 are made equal, so that it is possible to achieve the purpose that the lengths of the passages are made equal. The detail of a method for making the lengths from the multi-branch part 222 to the culture vessels 201 equal will be described later.

Figure 5A:
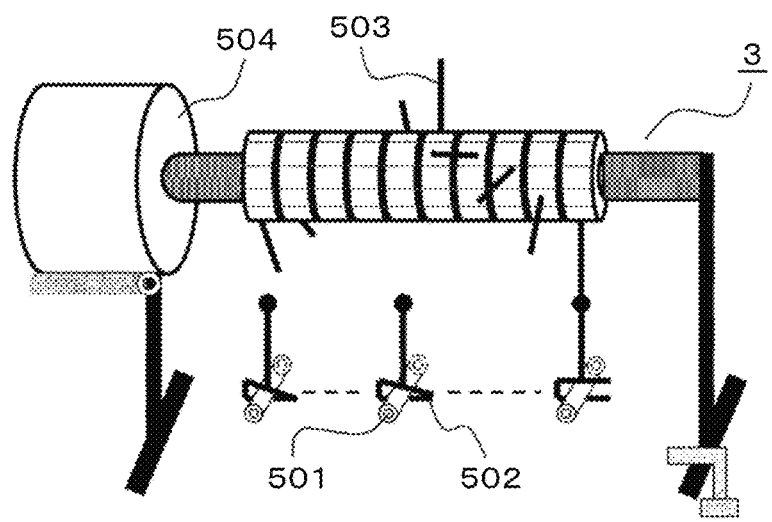
FIG. 5 is a diagram of an exemplary rotational valve mechanism included in the passage circuit according to the first embodiment.
Figure 5B:
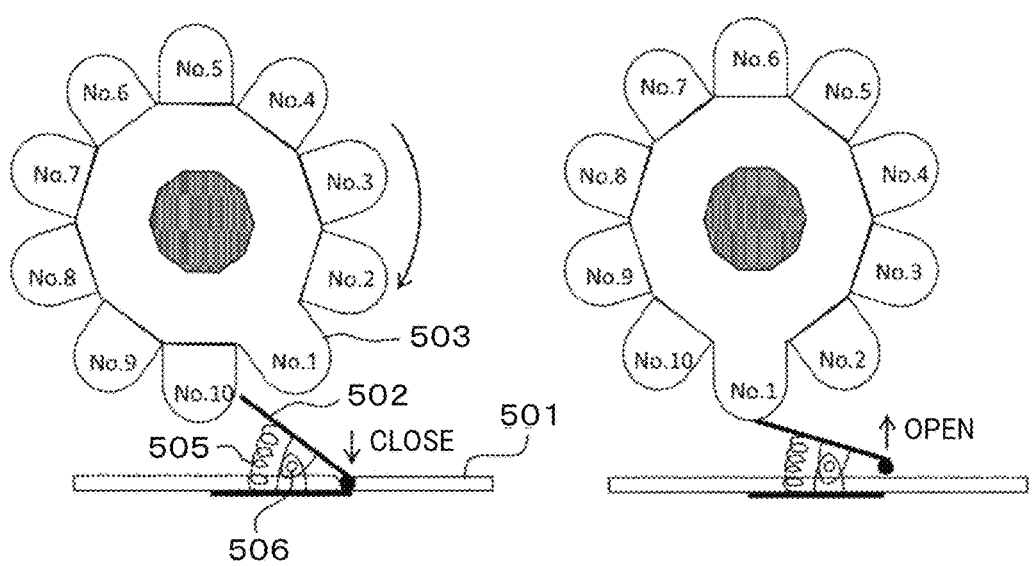

FIG. 5 is an example of the rotational valve mechanism as the liquid solution mechanism according to the embodiment illustrated in FIG. 1. However, the liquid solution mechanism according to the embodiment is not limited to this rotational valve mechanism. It is without saying that such a supply mechanism is applicable that the supply mechanism can control the supply of a liquid solution passed through the multi-branch part 222 to the individual culture vessel 201.

The rotational valve mechanism 3 illustrated in FIG. 5 collectively controls the supply of a culture medium or a gas to a plurality of the culture vessels 201 for cultivation at the same time. As illustrated in (A) on the upper part in FIG. 5, the rotational valve mechanism 3 includes a clip part 502 that is a valve mechanism for opening and closing a plurality of the passage tubes and for closing a passage tube 501, a multiple cam part 503 that opens the clip part 502 by contact, and an actuator 504 that rotates the multiple cam part 503. Moreover, as illustrated in (B) on the lower part in FIG. 5, the clip part 502 includes a spring 505 that closes a clip and a clip contacting part 506 that contacts the multiple cam part 503. Since the clip contacting part 506 can change a clip closed by the rotation of the multiple cam part 503, the direction of liquid delivery and gas supply can be controlled.

Moreover, two cell bottles 404 and 405 and the preheat bottle 406, described later, are located in the state in which the bottles are joined to the passage part through the passage tubes, and the bottles are disposed on a scale, not illustrated, in the passage part 2. For the cell bottles 404 and 405, the amounts of liquid delivery are confirmed from changes in the weight after liquid delivery to the culture vessels 201 when cell suspensions are delivered. The amount of liquid delivery is controlled by operation hours of the tube pump, and a change in the weight is also monitored, so that the amount of liquid delivery is more reliably grasped. Similarly, the amount of liquid delivery from the preheat bottle 406 is also grasped by two items, operation hours of the tube pump and a change in the weight.

FIG. 6 is examples of the cell bottle, the preheat bottle, and the humidification bottle of the liquid solution holding part included in the passage circuit of the device according to the embodiment. In the case of a cell bottle 601, in the cultivation of epithelial cells as described above, two bottles corresponding to epithelial cells and feeder cells are used. As illustrated in (A) on the left side in FIG. 6, the cell bottle 601 according to the embodiment includes a cell bottle main body part 602 and a cell bottle cover part 603. The cell bottle cover part 603 is mounted with a liquid delivery passage tube 604 and an internal pressure adjustment passage tube 605, and one ends of the tubes are provided in the inside of the cell bottle main body part 602. The end of the liquid delivery passage tube 604 on the cell bottle side contacts the bottom face of the cell bottle main body part 602. Thus, when a liquid is delivered, a liquid can be delivered even though the amount of a cell suspension becomes small as the process of liquid delivery progresses. It is possible to use a cell suspension efficiently. As a result, the amount of cells extracted from a patient is decreased, and a burden on the patient is decreased.

A sterile connecting part 606 is mounted on the end on the opposite side of the cell bottle on the liquid delivery passage tube 604. The end of the internal pressure adjustment passage tube 605 on the cell bottle side is located on the portion to be a gaseous phase when the cell suspension is put into the cell bottle main body part 602. A filter 607 is mounted on the end on the opposite side of the cell bottle side of the internal pressure adjustment passage tube 605; and a such a filter is used in the quality that a particle having a particle size of 0.22 μm or greater, for example, is not passed.

For the culture medium bottle built in the refrigerator, one bottle is used because a culture medium is in common in two kinds of cells as described above. The culture medium bottle is in a configuration the same as the cell bottle 601 as described above, and a culture medium is put into the culture medium bottle for use instead of a cell suspension. The culture medium is stored in the refrigerator at low temperatures at a temperature of 4° C., for example, in order to prevent the degradation of a growth factor and the like in the culture medium.

As illustrated in (B) in the center in FIG. 6, the preheat bottle part according to the embodiment includes a preheat bottle 608 and a receiving part 609. Although the culture medium is stored at a temperature of 4° C. until the culture medium is used, the culture medium is pre-heated at the preheat bottle part 6 before culture medium replacement because cultivation is performed at a temperature of 37° C. In this method, the temperature control of a heater is unnecessary as compared with the case where a heater or the like is used for pre-heating, and it is possible to avoid an increase in the number of components and an increase in the lengths of the passage tubes. The preheat bottle 608 includes a preheat bottle main body part 610 and a preheat bottle cover part 611. The portion around the preheat bottle 608 is surrounded by the receiving part 609 formed of a material of a high thermal conductivity such as aluminum. The preheat bottle cover part 611 is mounted with a supply passage tube 612 and a liquid delivery passage tube 613, and one ends of the tubes are located in the preheat bottle main body part 610. The end of the liquid delivery passage tube 613 on the preheat bottle side contacts the bottom face of the preheat bottle main body part 610. Thus, a liquid can be delivered even though the amount of the culture medium in the preheat bottle is decreased when a liquid is delivered. The end of the supply passage tube 612 on the preheat bottle side is located on the portion to be a gaseous phase when the culture medium is put into the preheat bottle main body part 610. The preheat bottle is disposed on the back of the cell bottle, for example. Since the weights of the cell bottle and the preheat bottle are both measured when a liquid is delivered, it may be fine that all the bottles are placed on the same scale as necessary and the space for disposing the scale is decreased.

As illustrated in (C) on the right side in FIG. 6, the humidification bottle part according to the embodiment is formed of a humidification bottle 614. The humidification bottle 614 includes a humidification bottle main body part 615 and a humidification bottle cover part 616. The humidification bottle cover part 616 is mounted with an air supply passage tube 617 and an air supply passage tube 618, and one ends of the tubes are located in the humidification bottle main body part 615. The end of the air supply passage tube 617 on the cell bottle side is located on the portion to be a gaseous phase when sterilized water is put into the humidification bottle main body part 615. Moreover, a filter 619 is mounted on the end on the opposite side of the humidification bottle side of the air supply passage tube 617. For the filter 619, such a filter is used in the quality that a particle having a particle size of 0.22 μm or greater, for example, is not passed. A sterile connecting part 620 is mounted on the outer side of the filter 619. It is noted that for the position at which the filter is mounted, it is fine that the filter is mounted at a given position between the sterile connecting part 620 and the gas supply part 10.

The end of the air supply passage tube 618 on the humidification bottle side contacts the bottom face of the humidification bottle main body part 615. The purpose of the humidification bottle is to saturate moisture in a supplied gas. Therefore, when the time to contact sterilized water is prolonged, the efficiency to saturate a gas is improved. Moreover, it may be fine that a filter is disposed on the end of the air supply passage tube 618 on the humidification bottle side to make fine bubbles. Since this causes an increase in the surface area, the efficiency of saturation is improved similarly. On the end of the air supply passage tube 618 on the opposite side of the humidification bottle side, a connecting part 621 is disposed and used for the connection of the gas supply part 10.

The discharge bag part 7 according to the embodiment illustrated in FIG. 1 recovers a waste fluid that is an old culture medium used for cultivation. In the passage according to the embodiment illustrated in FIG. 2, waste fluids on the upper layer and the under layer of the culture vessel 201 are separated, and the waste fluids are collectively recovered all the replacements of the culture media. As described above, the culture media on the upper layer and the under layer are separated for recovery every time when the culture medium is replaced, so that it is possible to analyze culture medium components on the individual layers and to determine whether cells are normally cultured in the process of cultivation. It is noted that in FIG. 1, the discharge bag 7 is provided in the inside of the accommodation housing. In the case where the components of a waste fluid are analyzed, it may be fine that the discharge bag 7 is also stored in the refrigerator to maintain the quality of the waste fluid.

Moreover, in the case where components of a waste fluid are not analyzed, it may be fine that the media on the upper layer and the under layer are not separated and the waste fluid is collectively recovered. In the recovery of the discharge bag in the midway point of cultivation, the sterile detachable part is introduced immediately before the discharge bag, and the discharge bag is removed in a sterile manner. Furthermore, in the drawing, although the solenoid valve is introduced immediately before the discharge bags, it may be fine that the rotational valve mechanism described above is introduced, or that a clip or the like, which does not need conduction and is manually handled, is introduced because of one time use.

Figure 7B:
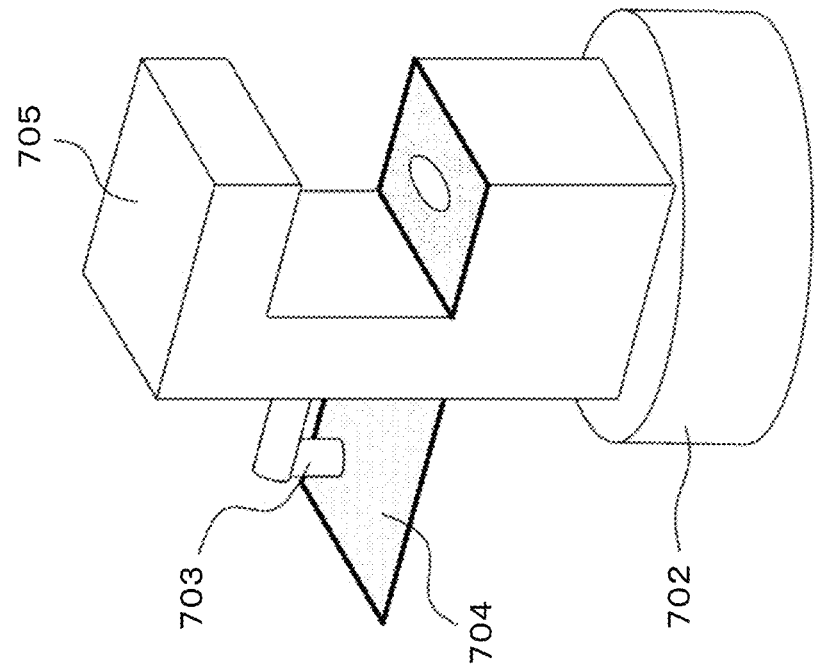
FIG. 7B is a diagram of an exemplary configuration of a microscope according to a seventh embodiment.
Figure 7A:
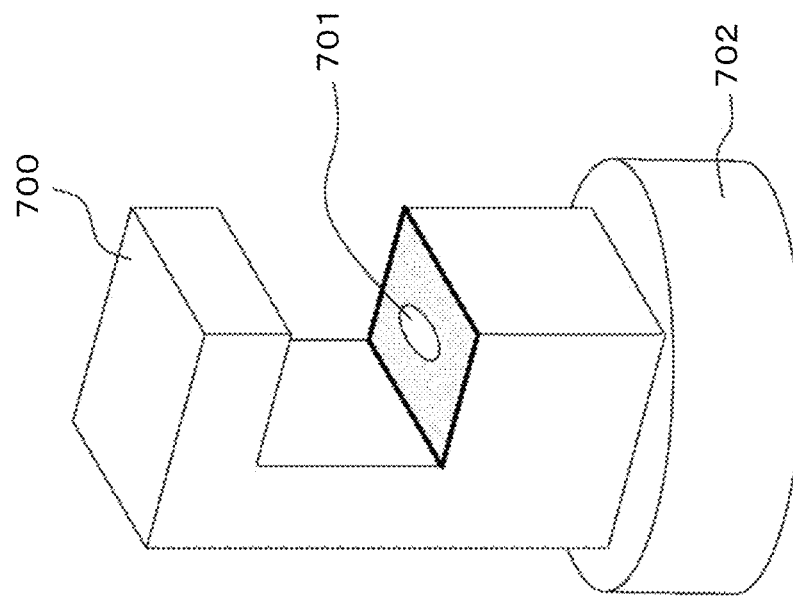
FIG. 7A is a diagram of an exemplary configuration of a microscope according to the first embodiment.

FIG. 7A is the case where a phase contrast microscope is used for the observation part of the device according to the embodiment. As illustrated in FIG. 7A, a phase contrast microscope 700 has an observation hole 701. Although omitted in FIG. 7A, an objective lens is included below the observation hole 701. Moreover, a lighting part, not illustrated, is included on the opposite side of the objective lens as the observation hole 701 is sandwiched.

In observation in the device, cells are not observed by moving a stage on which, the culture vessels are placed, and observation is made in which the rotation direction of the phase contrast microscope 700 is moved and the phase contrast microscope 700 is moved in the horizontal direction to the disposition surface with respect to the culture vessel base 202 on which the culture vessels 201 are disposed as described later. In the case where the culture vessels themselves are moved to and fro in the horizontal direction with respect to the disposition surface of the culture vessel base 202, a mechanism that moves the culture vessels independently is necessary to complicate the device. Moreover, since the passage tubes 303 are connected to all the culture vessels 201 all the time as illustrated in FIG. 3, when the culture vessels 201 are moved independently, the relative positions of the passage tubes with respect to the culture vessel base 202 are also changed, and the lengths of the passage tubes are prolonged accordingly, sometimes causing an increase in risks such as a loss of cells in seeding and the occurrence of damage to a cell membrane. Furthermore, the culture vessel itself is driven to twist the connected passage tubes, causing risks such as a loss of cells similarly to the described above.

Therefore, the device according to the embodiment adopts a method in which the phase contrast microscope 700 is moved with respect to the culture vessel base 202 as described above. In this method, the culture vessel base can be fixed and handled during cultivation, so that it is possible to avoid twisted passage tubes caused by the rotation of the culture vessel base for observation, for example, and it is possible to avoid the risks of damage to the passages.

As illustrated in FIG. 7A, the phase contrast microscope 700 includes an operating part 702 that is a drive part for operating on the culture vessel base 202. Therefore, the phase contrast microscope 0.700 can be rotated in the rotation direction and moved to and fro in the horizontal direction with respect to the disposition surface of the culture vessel base 202. It is noted that another exemplary configuration of microscopic observation illustrated in FIG. 7B will be described later in a sixth embodiment.

Figure 8A:
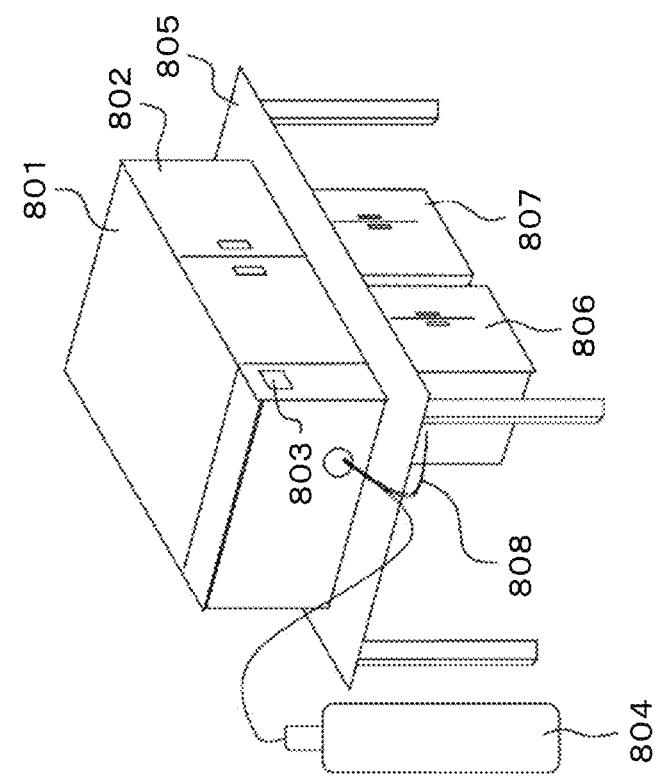
FIG. 8 is a schematic diagram of an example of the automatic culture device according to the first embodiment.
Figure 8B:
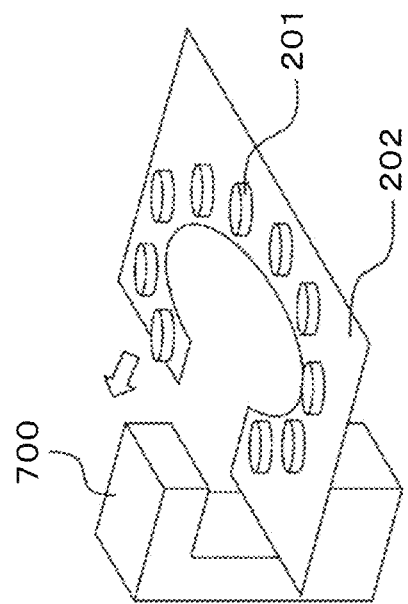

Subsequently, an exemplary layout of the passages and the microscope configuring the device according to the embodiment will be described with respect to FIGS. 8, 9, and 10. FIG. 8 is a state in which a door 802 of an incubator 801 of the incubator part in the automatic culture device. This example is an example of two doors opened from the center of the incubator 801 to the outer side. A surveillance monitor 803 is disposed on the incubator 801. The surveillance monitor 803 displays the temperature in the inside of the incubator and the operation status showing normality or abnormality of the solenoid valve, the tube pump, the microscope, and the like. The temperature in the inside of the incubator 801 is maintained at a temperature of 37° C.

As illustrated in the passage circuit depicted in FIG. 2, humidity control is unnecessary because a gas is directly supplied to the inside of all the culture vessels. As a result, since the devices in the incubator 801 are not exposed to a high humidity environment, the risks of faults caused by rust and the like due to humidity are decreased. Moreover, it is possible to use a HEPA filter (High Efficiency Particulate Air Filter) for internal air circulation. This is because the HEPA filter is not clogged because humidity is not high. Therefore, it is possible to realize higher cleanness as compared with the case where a typical filter is used.

A gas supply part 804 corresponding to the gas supply part 10 in FIG. 1 includes a gas cylinder and a gas flow controller. In this example, air including 5% of $CO_2$ is filled in the gas cylinder. Kinds of gasses to be filled can be changed according to a culture medium used for cultivation and a cell species for cultivation. When a gas is exchanged, a gas flow rate for supply is adjusted using the gas flow controller.

As illustrated in (A) on the left side in FIG. 8, the incubator 801 is provided on a desk 805, and a refrigerator 806 that stores the culture medium bottle at a temperature of 4° C., for example, and an accommodation housing 807 that stores the discharge bag on the discharge bag part 7 are provided below the desk. It is noted that it may be fine that various discharge bags are disposed on the refrigerator 806 configuring a bottle disposing part. In this case, the advantages of a reduction in the disposition area and a decrease in cost are obtained.

The incubator 801, the refrigerator 806, and the accommodation housing 807 are joined to one another through passage tubes 808. In other words, this means that the incubator 801 whose temperature is maintained at a temperature of 37° C. is not spatially close to the refrigerator 806 whose temperature is maintained at a temperature of about 4° C., and the incubator 801 is spaced from the refrigerator 806 in a space in the CPC air-conditioned at a temperature of about 25° C. generally. With this configuration, it is unnecessary to provide a high heat insulator between the incubator 801 and the refrigerator 806, and it is possible to decrease costs because of the simplification of the device configuration and to improve the performance of maintaining temperature.

Near the incubator 801, the control part 12 in FIG. 1 is disposed to operate the device. In the case where a plurality of the automatic culture devices according to the embodiment is operated in a parallel manner, one controller can control all the automatic culture devices. Moreover, a management monitor that allows management from the outside of the CPC is also disposed as necessary.

The components such as the passage part 2 and the culture vessel base 202 in the inside of the device are placed on mounting stages, not illustrated, connected to a rail, similarly not illustrated as well, disposed in the incubator 801, so that the components can be collectively drawn through the door 802 using the rail, similar not illustrated. When the user connects and disposes the passages on the passage part and the like when cultivation is started, for example, the components can be disposed in the state in which the mounting stages are drawn, so that it is possible to decrease complicatedness when the passages are disposed, and it is possible to suppress human errors by the user. In the disposing, it is desirable to unload a part of the passage part 2 and the microscope 700 of the observation part 8 from the inside of the incubator 801, not fully unloaded. Alternatively, it may be fine that the microscope 700 is fixed to the inside of the device. This is because such an event is avoided that the passage part and the microscope are dropped and damaged or that an operator is injured, due to the passage part and the microscope, which are heavy. It is noted that such a method may be fine that the portions to be removed from the incubator 801 are the passage part 2 and the culture vessel base 202 and the microscope is not removed. In this case, the drawing work is more facilitated as compared with the method described above because the number of the components is decreased.

FIG. 9 is an exemplary disposition configuration of the passage part and the microscope of the automatic culture device according to the embodiment. (A) on the left side in FIG. 9 is the three-dimensional disposition of the passage circuit illustrated in FIG. 2. First, the culture vessel base 202 is disposed in such a manner that culture vessels 201-1 to 201-10 are disposed around the microscope 700. Three actuators 901 support the culture vessel base 202, and operate to tilt the culture vessel base 202 when the culture medium is replaced. In this example, ten culture vessels 201 are disposed on the culture vessel base 202, and as described above, four passage tubes 302, two tubes for supply and a waste fluid on the upper layer and two tubes for supply and discharge on the under layer, are mounted per culture vessel 201.

A bundle 902 of the passage tubes is disposed on the outer circumferential side of the culture vessel base 202 from the culture vessel base 202 to a rotational valve mechanism 903 corresponding to the rotational valve mechanism 3 in FIG. 1 in order not to block the drive of the microscope 700 as discussed above. The bundle 902 of the passage tubes includes 20 passage tubes for the supply of various liquid solutions to the culture vessel and 20 passage tubes for discharge in a bundle. It is noted that although the detail will be described later in a second embodiment, it is also possible that the bundle 902 of the passage tubes is disposed on the inner circumferential side of the culture vessel base 202 from the culture vessel base 202 to the rotational valve mechanism 903. In this case, the sterile detachable part is also disposed on the inner circumferential side of the culture vessels.

The rotational valve mechanism 903 is located on a rotational valve mechanism stage 904, and 40 passage tubes are disposed on the rotational valve mechanism stage 904. The bundle 902 of the passage tubes is located near the center of 40 passage tubes arranged at the rotational valve mechanism 903 in order to uniformize the lengths of the passage tubes as the user easily handles the passage tubes in a bundle. In addition, ten culture vessels on the culture vessel base 202 are disposed in symmetry to the bundle 902 of the passage tubes. Thus, it is possible to minimize the difference of the distance between the culture vessel 201 located at the farthest position from the rotational valve mechanism 903 and the culture vessel located at the closest position. In order to uniformize cells after manufactured in a plurality of the culture vessels, it is desirable to equally align the lengths of the passage tubes to the culture vessels. More specifically, the lengths from the multi-branch part at which one passage tube is branched to ten tubes to the culture vessels are made equal.

The multi-branch part 222 described in FIG. 2 is disposed between the rotational valve mechanism 903 and the passage part 2. When the description is made with reference to FIG. 2 described above, in the passage circuit, the lengths of ten passage tubes from the multi-branch part 222, at which the cell suspension of epithelial cells is branched into a plurality of the passages (the case of ten passages in this example), to the culture vessels 201 are made equal. Moreover, similarly, the lengths of ten passage tubes from the multi-branch part, not illustrated, at which the cell suspension of feeder cells is branched, to the culture vessels 222 are made equal.

For the lengths of the passage tubes to the culture vessels 201, which are made equal, since the distance from the rotational valve mechanism 903 is varied depending on the culture vessels, it is desirable to align the lengths of the passage tubes to the length of the passage tube of the culture vessel at the furthest position from the rotational valve mechanism 903. For example, in the case where the rotational valve mechanism 903 is disposed on the door part side of the device as in the embodiment, it is desirable to align the lengths of the passage tubes connected to the other culture vessels to the length of the passage tube connected to the culture vessel disposed at the position on the most rear side of the device seen from the door part side.

As described above, in order to uniformize cells after manufactured in a plurality of the culture vessels 201, it is important to align the lengths of the passage tubes to the culture vessels 201. However, in order to provide regenerated tissue after manufactured in high quality, it is desirable to provide a configuration in which the passage tubes in equal lengths are the shortest among the culture vessels.

Here, a configuration will be described in which in order to uniformize and minimize the lengths of the passages in the case where the culture vessel base 202 in a so-called U-shape is used as in the embodiment. In the embodiment, as depicted by an arrow in (B) on the right side in FIG. 8, the culture vessel base 202 is inserted into the cabinet of the device from the notch side provided on the culture vessel base 202 through the door 802 illustrated in (A) on the left side in FIG. 8 in order to guide the microscope 700 to the vacant space portion so as not to cause the culture vessel base 202 to contact.

Moreover, as illustrated in (A) on the left side in FIG. 9, the rotational valve mechanism 903 is disposed on the door part side and below the culture vessel base 202. The reason why the rotational valve mechanism 903 is disposed on the door part side is that the user easily mounts the passages and the like on the rotational valve mechanism 903, for example. Furthermore, the reason why the rotational valve mechanism 903 is disposed below the culture vessel base 202 is that the rotational valve mechanism 903 does not become an obstacle in inserting the culture vessel base 202 into the device.

According to the configuration described in detail above, it is the notch portion that is located in the furthest distance from the rotational valve mechanism 903, the notch portion at which the culture vessel 201 is not enabled to be disposed on the culture vessel base 202. In other words, the culture vessel 201 is not disposed on the extension line in the direction from the rotational valve mechanism 3 side to the microscope 700 side.

In other words, with the configuration described above, such a configuration can be provided in which the culture vessel 201 is not disposed at the position the furthest from the rotational valve mechanism 903. Therefore, the culture vessel 201 at the furthest position from the rotational valve mechanism 903, which is the reference to uniformize the lengths of the passages, is the culture vessels disposed closest to the notch portion as the culture vessels 201-1, 201-10, and so on.

When the rotational valve mechanism 903 is disposed at the position on the passage part side, for example, the notch portion does not exist at the furthest position from the rotational valve mechanism 903, that is, on the extension line in the direction from the rotational valve mechanism 903 side to the microscope 700 side, and such a configuration is formed in which the culture vessel is disposed on the side opposite to the rotational valve mechanism 903 through the microscope 700. Therefore, since this culture vessel is a reference to uniformize the lengths of the passages, the lengths of the passages are longer than in the configuration according to the embodiment.

Therefore, the culture vessel base 202 is disposed in such a manner that the notch portion is located at the furthest from the rotational valve mechanism 903 as in the embodiment, it is possible to uniformize cells manufactured in the culture vessels and to provide higher quality as compared with the other disposition relationships.

On the bundle 902 of the passage tubes illustrated in (A) on the left side in FIG. 9, a jig 905 that aligns the passage tubes for the individual culture vessels and for individual purposes is disposed between the rotational valve mechanism 903 and the culture vessel base 2 as a part that bundles the passages as illustrated in (B) in on the right side in FIG. 9, so that complicatedness in the attachment and detachment of the culture vessel base 202 in the inside of the device is solved, and the presence or absence of interconnection errors in manufacture is more easily confirmed.

20 passage tubes for the supply to the culture vessel 201 are branched for the individual cell species for one each. In other words, a single passage tube 403 for the supply of various liquid solutions from the cell bottle 404 including epithelial cells to the upper layer of the culture vessel 201 through the solenoid valve 402 and the tube pump 401 is divided into ten tubes at the multi-branch part 222. The same thing is applied to the cell bottle 405 including feeder cells. Although not illustrated in FIG. 9, a culture medium is delivered from the culture medium bottle stored in the refrigerator at a temperature of 4° C. to the preheat bottle 406, and is delivered to the culture vessels 201 after preheated.

The passage tubes from two cell bottles 404 and 405 are branched into ten each at the multi-branch part 222, and the lengths from the multi-branch part 222 to the culture vessels 201 are equal as described above. Thus, it is possible that the liquid-feeding conditions when cells are seeded and when the culture medium is replaced is made equal. Suppose that the lengths of the passages to the culture vessels are made uniform, the distance from the multi-branch part at which a single passage is branched into ten passages to the culture vessels is varied for the individual culture vessels, and it may be fine that in the lengths of the passages from the multi-branch part to the culture vessels, a passage tube having a length to be a difference is disposed as an adjustment passage in an adjustment passage disposing region provided in the device.

Figure 10A:
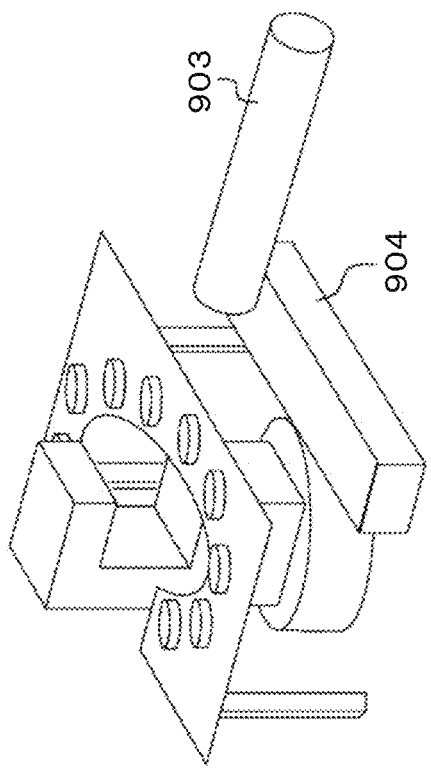
FIG. 10 is a diagram of an exemplary passage of the automatic culture device according to the first embodiment.
Figure 10B:
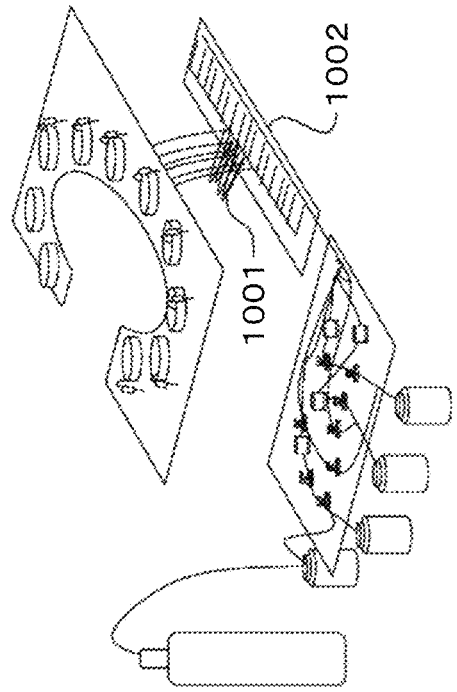
Figure 11A:
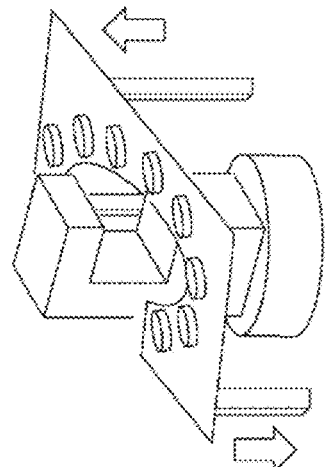
FIG. 11 is a diagram of an example of the motions of the microscope and a passage base of the automatic culture device according to the first embodiment when cells are seeded, a culture medium is replaced, and cells are observed.
Figure 11B:
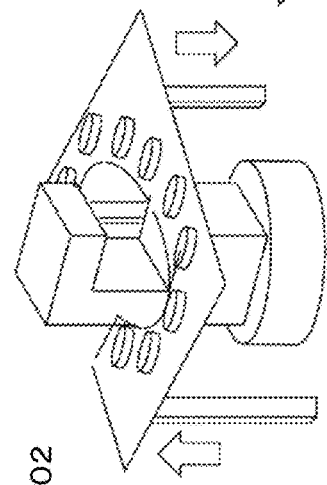
Figure 11C:
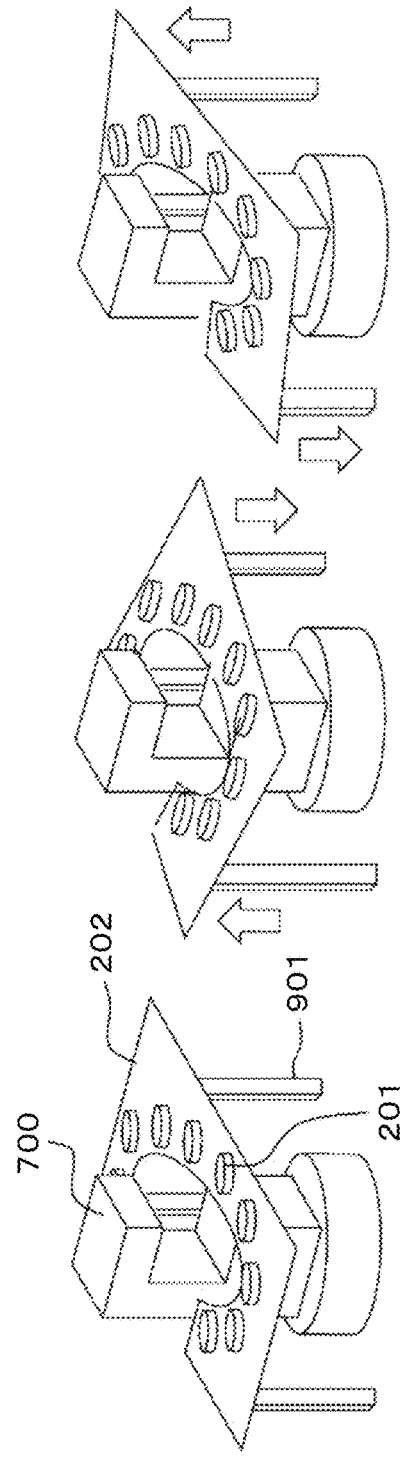
Figure 11E:
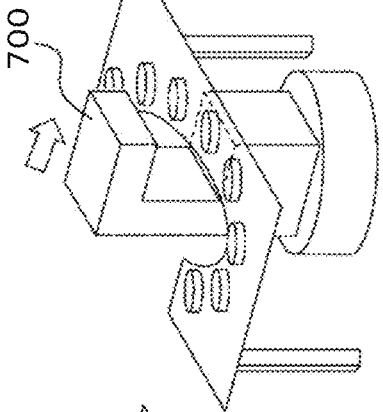
Figure 11F:
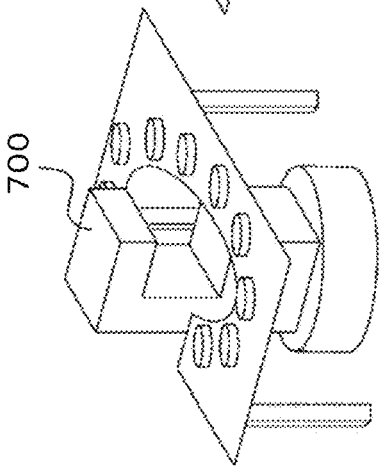
Figure 11D:
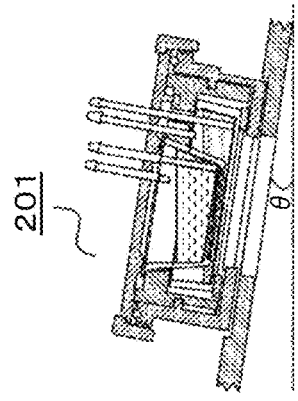

FIG. 10 is a diagram of the three-dimensional configuration of only a portion related to the passages of the device according to the embodiment and the state of the device when the passages are disposed. When the passage tubes are disposed in such a manner that the passage tubes are straight lines according to the distance from the multi-branch part to the culture vessels, the difference between the length of the passage tube and the distance is produced as the bending of the passage tube. An adjustment passage 1001 illustrated in (A) on the left side in FIG. 10 is the portion that the bending is bundled. In order not to receive the influence of potential energy at the adjustment passage 1001 when a liquid is delivered, the adjustment passage 1001 is disposed in such a manner that the passage tubes are provided on the same plane. Thus, it is possible to suppress the influence on the liquid delivery velocity caused by a difference in potential energy, for example. Moreover, as long as the position of the adjustment passage 1001 is disposed between the multi-branch part and the culture vessels, the purpose of making the distances to the culture vessels equal is achieved. As discussed above, although it is desirable that the passage tubes configuring the adjustment passage 1001 be located on the same plane, it is most desirable that the plane on which the passage tubes are disposed be a plane on which the rotational valve mechanism 903 is disposed. Since the rotational valve mechanism 903 is located below the culture vessel base 202 at which the user works and is out of the drive range of the microscope 700, the rotational valve mechanism 903 is at the position at which the rotational valve mechanism 903 is not an obstacle in cell cultivation. It is noted that the region on which the adjustment passage 1001 is disposed is sometimes referred to as an adjustment region.

The passage tubes disposed on the rotational valve mechanism 903 are disposed on a transparent, light-weight rotational valve mechanism disposition plate 1002 similarly to the description above. Since the rotational valve mechanism 903 controls the opening and closing of 40 passage tubes for the supply and discharge of various liquid solutions from the culture vessels, the passage tubes are properly aligned. With this configuration, it is possible to suppress the risks of faulty connections when the user connects the passage tubes.

As illustrated in (A) on the left side in FIG. 9, the rotational valve mechanism 903 is located on the rotational valve mechanism stage 904. When the rotational valve mechanism disposition plate 1002 is disposed, the rotational valve mechanism 903 is rotated in the horizontal direction with respect to the rotational valve mechanism stage 904 as illustrated in (B) on the right side in FIG. 10. It is without saying that it is also possible that the rotational valve mechanism 903 is rotated in the vertical direction as another embodiment. However, the rotation in the horizontal direction can suppress risks that an operator is injured in the case where the rotational valve mechanism bangs when the rotational valve mechanism disposition plate disposed.

FIG. 11 is the motion of the culture vessel base immediately after cells are seeded and when the culture medium is replaced and the motion of the microscope when cells are observed in the device according to the embodiment. First, as illustrated in (A) to (D) in FIG. 11, the disposition angle of the culture vessel base 202 to the horizontal plane is changed using three actuators 901. When cells are seeded, it is possible to uniformize the distribution of cells in the culture vessels 201 by rocking the culture vessel base 202. Moreover, such an effect is also exerted that the culture vessel 201 is tilted to deliver a liquid to suppress the production of bubbles in the vessels. Furthermore, as illustrated in (D) in a cross sectional view in FIG. 11, in disposition replacement, the culture vessel 201 is tilted to the outlet port side at an angle θ, and the discharge efficiency of the culture medium is improved. In (E) and (F) in FIG. 11, the motion of the microscope 700 is schematically illustrated by an arrow when cells are observed. When cells are observed, the microscope is rotated and driven to and fro with respect to the culture vessels 201 on the culture vessel base 202.

FIG. 12 is another exemplary device configuration for making the lengths of the passages from the multi-branch part to the culture vessels equal in the device according to the embodiment. It is noted that as discussed above, it is desirable that the passage tubes be in the equal length while decreasing the lengths of the passages from the multi-branch part, from which epithelial cells and feeder cells are delivered, to the culture vessels as much as possible for the lengths of the passages. In (A) to (D) in FIG. 12, the microscope 700, the rotational valve mechanism 902, the passage part 2, and the culture vessel base 202, which are main components of the device, are illustrated, and the other components are omitted.

In the layout in (A) in FIG. 12, since the rotational valve mechanism 902 is disposed on the floor of the incubator part, it is possible to avoid complicatedness when the passages are disposed. In (B) in FIG. 12, the rotational valve mechanism 902 is disposed on the lateral side of the culture vessel base 202. Although the disposition stage is necessary because the rotational valve mechanism 902 is not disposed on the floor of the incubator, such an advantage can be obtained that the breath of the device is smaller as compared with the configuration in (A) in FIG. 12. In (C) in FIG. 12, the rotational valve mechanism 902 is disposed on the microscope 700. Although the disposition stage is further necessary because the rotational valve mechanism 902 is not disposed on the floor of the incubator, the breath of the device is smaller than in (A) and (B) in FIG. 12, and as a result, the disposition area is also decreased. In (D) in FIG. 12, the rotational valve mechanism 902 is disposed on the side of the microscope 700. Therefore, the rotational valve mechanism 902 is easily disposed, and such an advantage can be obtained that the lengths of the tubes from the cell bottle to the culture vessels are further shortened.

Figure 13:
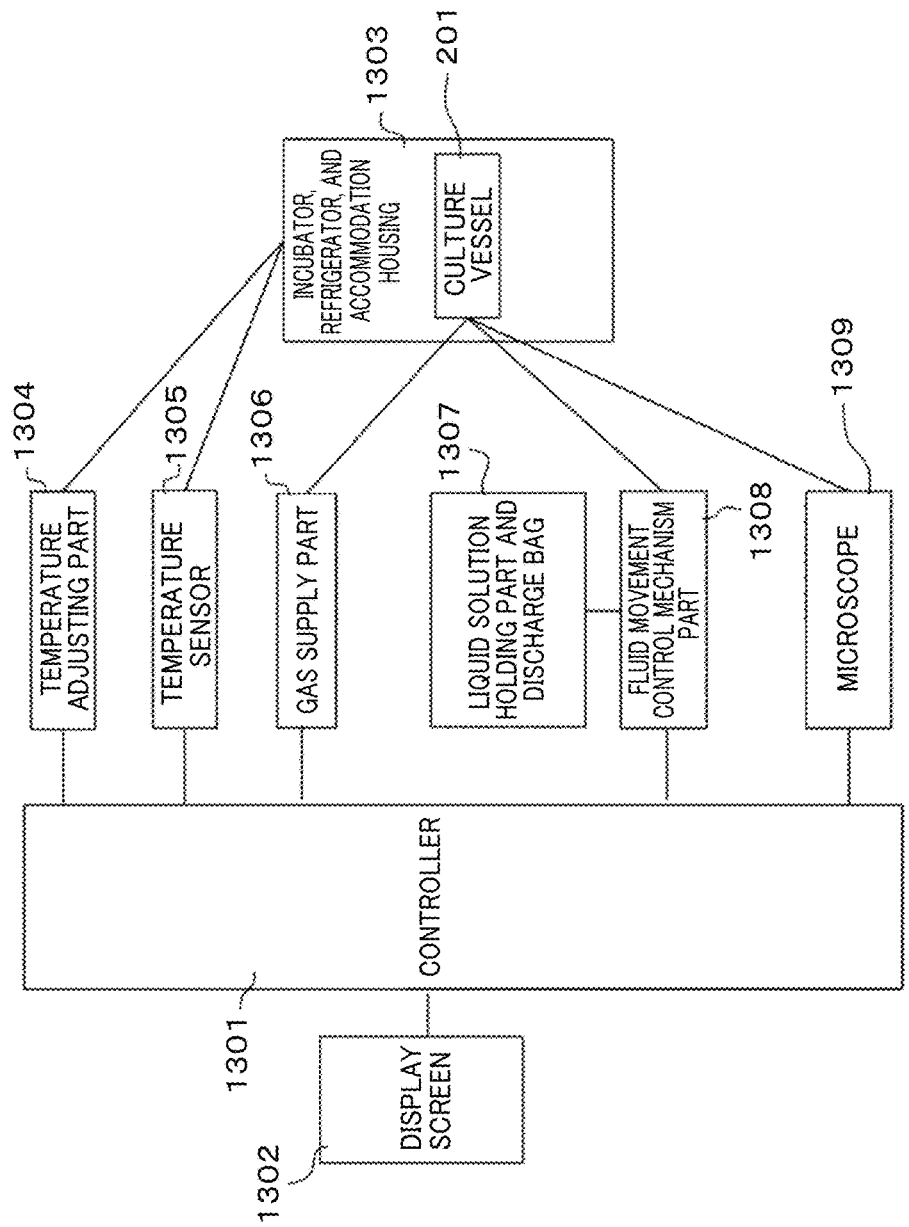
FIG. 13 is a block diagram of a control mechanism of the automatic culture device according to the first embodiment.

Subsequently, an exemplary control mechanism of the automatic culture device according to the embodiment as described above will be described. First, FIG. 13 is a functional block diagram of the functional configuration of the automatic culture device described above. The components controlled by a controller 1301 corresponding to the control part in FIG. 1 are disposed in the inside of an incubator part, a refrigerator, and an accommodation housing 1303, and connected to the culture vessels 201. It is noted that the incubator, it is without saying that the components disposed in the inside of the incubator, and the accommodation housing 1303 are the culture vessels disposed in the automatic culture device.

In FIG. 13, the controller 1301 is connected to a temperature adjusting part 1304 that controls the temperatures of the incubator, the refrigerator, and the accommodation housing 1303, a temperature sensor 1305, a gas supply part 1306 that supplies gasses to the inside of the culture vessels corresponding to the gas supply part 10 described above, a cell bottle, a culture medium bottle, a preheat bottle, and a discharge bag 1307, a fluid movement control part 1308 that automatically delivers a liquid and a gas in the passages corresponding to the passage part 2 described above, and a microscope 1309 for observation corresponding to the microscope 700 described above.

A controller 1302 and a display screen 1310 corresponding to the control part 12 and the control terminal 12 described above correspond to the processing part and the storage part of a typical computer including a processing part formed of a CPU (Central Processing part), a storage part, and an input/output part and the like formed of a display device and a keyboard, and to the display part of a display device. The controller 1302 operates various programs stored on the storage part on the CPU that is the processing part. Thus, the cultivation environment in the incubator 1303 is controlled using the temperature adjusting part 1304, the gas supply part 1305, the fluid movement control mechanism part 1308, the microscope 1309, the liquid solution holding part, and the discharge bag 1307, and predetermined cultivation processes can be performed in the culture vessel 1301.

Figure 14:
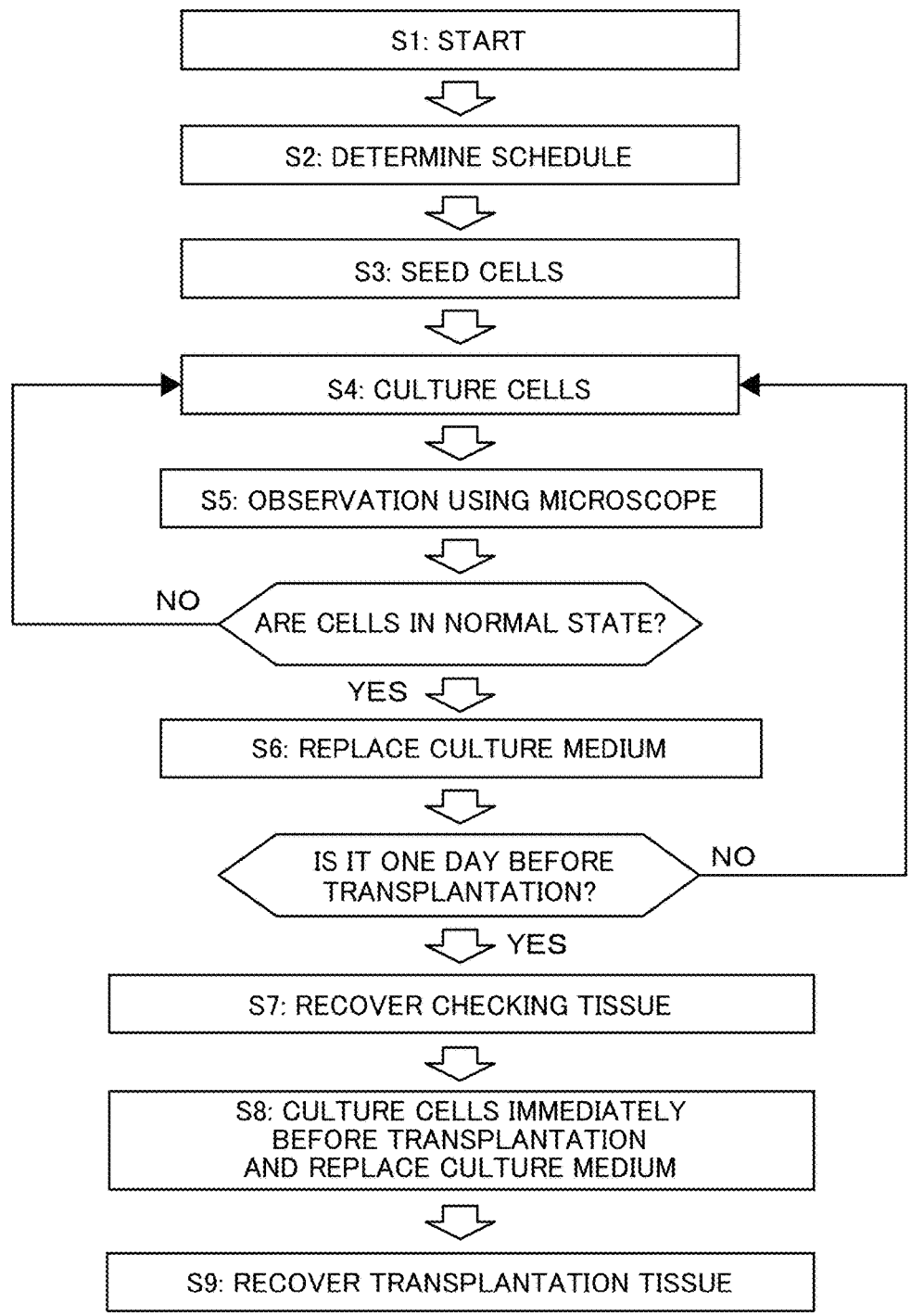
FIG. 14 is a flowchart of a cultivation protocol of the automatic culture device according to the first embodiment.

A series of cultivation procedures will be described when cells are cultured using the automatic culture device according to the embodiment having the configuration described above. FIG. 14 is a flowchart illustrative of the operation of the automatic culture device. In the following, the operation of the automatic culture device according to the embodiment will be described with reference to FIG. 14. It is noted that in the case where the number of the culture vessels for use is increased, it is fine that the culture vessels are arranged in a parallel manner at the branch part of the passages. It is fine that in the cultivation procedures, manipulations shown below are in turn performed on the culture vessels.

<Step S1: Start>

The automatic culture device is started. The operator presses the start switch of a manipulating part on the controller to start the device. On the manipulation screen of the display of the control part 12, the values of the internal environment of the automatic culture device are displayed.

<Step S2: Determine Schedule>

An automatic culture schedule performed on the automatic culture device is inputted as matched with the type and amount of cells to be cultured. The conditions of dates and time, frequencies, liquid amounts, and the like for manipulations such as cell seeding, culture medium replacement, microscopic observation, waste fluid recovery, checking tissue recovery, and transplantation tissue recovery are inputted through the control terminal 13 and the like connected to the control part 12.

<Step S3: Seed Cells>

After appropriately opening and closing the solenoid valve, the tube pump is operated, and a cell suspension is sucked from the cell bottle. Since oral epithelial cells are cultured in an example of esophagus engineering, a cell suspension is oral epithelial cells suspended in a KCM culture medium (keratinocyte culture medium) and 3T3-J2 cells, NIH-3T3 cells, or the like similarly suspended in the KCM culture medium. The cell suspensions are included in different cell bottles.

When cells are seeded, cell suspensions are delivered to the culture vessels 201 from two cell bottles. The solenoid valves joined to the culture vessel and the passage targeted for liquid delivery are opened beforehand, and are in the state in which liquid delivery can be performed. On the other hand, the solenoid valves joined to the culture vessels and the passages, not targeted for liquid delivery, are closed and in the state in which liquid delivery is not performed. Cells are in turn seeded on the upper layers and the under layers of ten culture vessels.

As described above, epithelial cells are passed through the passage circuit (1) depicted by a solid line in FIG. 2, and in turn seeded on the upper layers of ten culture vessels. Feeder cells are passed through the passage circuit (2) depicted by a broken line, and in turn seeded on the under layers of ten culture vessels. It is noted that the cell suspensions are sucked and discharged immediately before liquid delivery, and the distribution of cells in the cell bottles is uniformized, and the cell concentrations of the cell suspensions for delivery are made equal. After finishing seeding to all the culture vessels, the actuators 901 below the culture vessel base 202, on which the culture vessels are disposed, are operated. Although the culture vessels in cell seeding and cell cultivation are maintained horizontally, the culture vessels are tilted immediately after cells are seeded and when the culture medium is replaced. When cells are seeded, the culture vessels are continuously rocked to uniformize the distribution of cells. After rocking, the culture vessels are returned horizontally, and cells are cultured in this state.

<Step S4: Culture Cells>

In the state in which the culture vessels 201 stand horizontally, cells are cultured for a predetermined time. For example, in the case of oral epithelial cells, the period for standing is about three days after seeding. During cultivation, the inside of the culture vessels is maintained at a temperature of 37° C. in the incubator. The air in the device is stirred all the time using a fan, and the temperature distribution is uniform all the time. It is noted that in this example, although not illustrated, a particle counter or a viable cell count measuring device is mounted on the inside of the device, the cleanness is monitored, and the safety of manufacture is improved.

Moreover, during cultivation and immediately after cells are seeded, gas exchange is performed in which a gas having a predetermined component is supplied to the inside of the culture vessels. Gas exchange is performed even at a frequency about several times in a day during the cultivation period. Furthermore, in the case where oral epithelial cells are cultured, air including 5% of $CO_2$ concentration is supplied to the inside of the culture vessels. The gas is a gas that the air is supplied from the gas supply part, and passed through the humidification bottle part 11 before supplied to the culture vessels to saturate water molecules. Thus, it is avoided that moisture is evaporated from the culture medium in the culture vessels to change the culture medium component consequently. Moreover, the gas is directly supplied from the air supply circuit in parallel with the tube pump to the culture vessels using a gas pressure, not through the tube pump. Thus, the gas supply velocity can be more increased than in the case of the supply through the tube pump, and the efficiency of gas exchange is improved. Furthermore, a load on the tube pump is eliminated. An unnecessary gas after supplied to the culture vessels is discharged to the outside of the passages through a filter. In addition, an atmospheric pressure in the inside of the passages is adjusted through a filter as necessary. For the filter, such a filter is used in the quality that a particle having a particle size of 0.22 μm or greater, for example, is not passed.

Moreover, in the culture vessel 201 used in the device according to the embodiment, the passage tubes used for liquid delivery are not distinguished from the passage tubes used for gas supply. In other words, the passage tubes used for liquid delivery also serve as the function of gas supply. In the case of this configuration, the number of the passage tubes connected to the culture vessel is decreased, as compared with the case where the passage tubes used for liquid delivery and the passage tubes used for gas supply are separately provided. As a result, the simplification of the passages can be realized.

<Step S5: Observation Through Microscope>

A cell image is acquired using the microscope disposed in the automatic culture device. The light source disposed in the automatic culture device is appropriately illuminated, and the focus is achieved on cells using the microscope for imaging. Given fixed points are determined on the cultivation surface as necessary for imaging. The acquired cell image is stored on a database, and watched on the control terminal disposed on the outside of the device. Determination is made from information about the growth state of cells obtained from microscopic observation, and frequencies and timing for culture medium replacement are adjusted. For example, in the case where the attachment of cells is inadequate, culture medium replacement in S6 is not performed, and cell cultivation in S4 is continued.

The user appropriately manually manipulates the microscope 700, and observes and takes cells other than in automatic imaging of cells. The taken image can be stored similarly in the automatic imaging of cells.

<Step S6: Replace Culture Medium>

Culture medium replacement is performed at frequencies once a few days during the cultivation period. First, a culture medium stored in the refrigerator at a temperature of 4° C. is delivered to the preheat bottle for pre-heating. The culture medium is heated by thermal conduction caused by contacting the receiving part disposed around the preheat bottle and a gaseous phase in the incubator at a temperature of 37° C. For example, the culture medium is pre-heated for a few hours to about a day to increase the temperature at a temperature of 36° C. or greater, and the culture medium is used for culture medium replacement.

Subsequently, an old culture medium is discharged from the culture vessel 201. The culture vessels are tilted to the outlet port side using the actuators to discharge the entire amount of the old culture medium. After discharging, a pre-heated new culture medium is quickly supplied to the inside of the culture vessels. Thus, drying cells and a decrease in the temperature of cells on the cultivation surface are avoided. The old culture medium is finally discharged to the discharge bag part 7. It is assumed that an old culture medium is used for the analysis of culture medium components, and the old culture medium is recovered in the state in which the old culture medium is separated into the upper layer and the under layer of the culture vessels in the embodiment.

It is noted that in cell seeding and culture medium replacement described above, the cell suspension and the culture medium flow in one direction in the passage circuit illustrated in FIG. 2. In other words, the old culture medium used for cultivation is not mixed with the new culture medium not used for cultivation in the culture vessels. In the old culture medium and the new culture medium, since the amount of glucose consumed by cells is different from the amount of lactic acid produced by cells, for example, this means that the mixture of both media causes a change in the cultivation environment when the culture medium is replaced. On the contrary, with the configuration of the device according to the embodiment, the mixture of both media is prevented, so that it is possible to obtain the effect of improving the reproducibility of cell cultivation. Moreover, in the case where the culture medium component of the discharged old culture medium is analyzed, the new culture medium is prevented from being mixed with the old culture medium, so that it is possible to obtain the effect of improving the accuracy of analyzing the culture medium component.

<Step S7: Recover Checking Tissue>

In consideration of the situations of cell cultivation observed through the microscope 700, one culture vessel is unloaded from the device in a sterile manner for testing to determine whether to do transplantation. It is noted that it may be fine that the number of the culture vessels to be unloaded for testing as necessary is plural numbers. For unloading, the sterile detachable part disposed in the passage tube near the culture vessels is used. The sterile detachable part is a thermally weldable passage tube, for example, and a portion between two places including a cut place is cut after thermal welding. Thus, it is possible to maintain sterility in the inside of the removed culture vessel, the inside of the culture vessel not removed, and the inside of the passage after removal. After unloaded, testing is performed on the unloaded culture vessels quickly, and it is determined whether to do transplantation.

<Step S8: Cultivation and Culture Medium Replacement Immediately Before Transplantation>

Similarly to Steps S4 and S6, cell cultivation and culture medium replacement are performed.

<Step S9: Recover Transplantation Tissue>

In the case where it is determined to do transplantation from the result of testing in Step 7, a message is shown on the display of the control part that cultivation is completed. After the displaying, similarly to Step S7, tissue is unloaded from the device in a sterile manner, carried to an operating room, and used for tissue engineering and treatment.

With the device configuration and the cultivation processes according to the first embodiment described in detail, such a configuration is provided in which the lengths of the passages from the culture vessel to the multi-branch part or to the cell bottle is shortened as short as possible and the lengths of the passages are equally aligned, so that it is possible to perform treatment using regenerated tissue that the quality of cells to be cultured in the culture vessels is made uniform. Moreover, with the configuration that the user can easily handle the components, it is possible to suppress human errors, and as a result, it is possible to improve the quality of cells.

Second Embodiment

In the automatic culture device according to the first embodiment, such a configuration is shown in which the passage tubes individually connected to the culture vessels are bundled using the jig, for example. In an automatic culture device according to a second embodiment, an embodiment will be described in which passage tubes are not bundled and individually separately disposed on the corresponding valves of a rotational valve mechanism.

Figure 23:
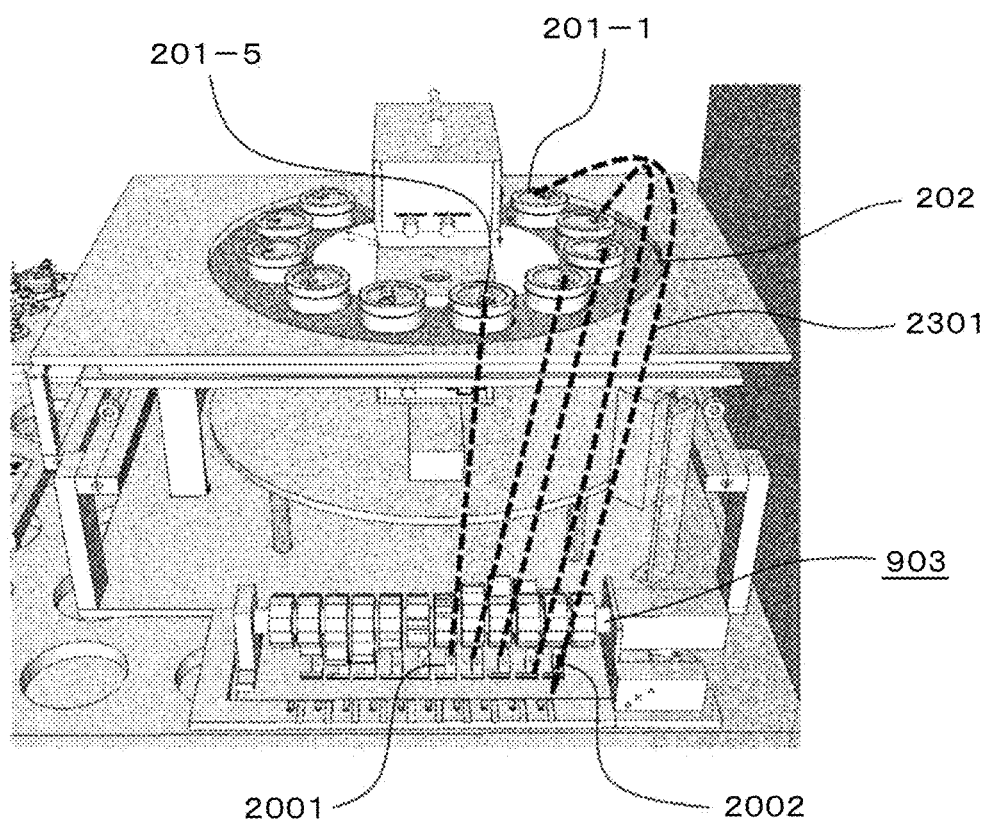
FIG. 23 is a perspective view of a culture vessel base inserted into a device according to the second embodiment.

FIG. 23 is a perspective view of an exemplary configuration of an automatic culture device according to the embodiment that can suppress the occurrence of crossing and twists of passages. In FIG. 23, for explanation, only passages on the right side of the culture vessel base 202 are illustrated. The passages are also similarly disposed on the left side of the vessel base 202. It is desirable that culture vessels 201 be in turn connected from the valve on the end side of the rotational valve mechanism 903 to a valve on the center side starting from the culture vessel 201-1 at the furthest distance from the rotational valve mechanism 903. In other words, the culture vessel 201-5 located at a place near the center seen from the door part side is connected to the grip of a valve 2001 provided at the position near the center of the rotational valve mechanism 903, and the culture vessel 201-1 disposed on the end side is connected to the grip of a valve 2002 provided on the end side.

In the case of the configuration according to the embodiment, it is desirable that the lengths of the other passages be matched with the length of a passage in the furthest distance from the multi-branch part similarly to the first embodiment. In other words, the lengths of the passages are made uniform relative to the length of a passage 2301 disposed on the grip of the valve 2002 on the endmost side of the rotational valve mechanism 903. At this time, for the adjustment passage connected on the same plane as the rotational valve mechanism 903, the adjustment passage becomes longer in the culture vessel disposed at the position in a closer distance from the center position of the rotational valve mechanism, that is, in a closer distance from the rotational valve mechanism, so that it is possible that the disposition area of the adjustment passage disposed on the adjustment region is more increased and the disposition area is more decreased as going to the end. This is because the length of the passage to be retracted is shorter as the distance from the grip of the valve of the corresponding rotational valve mechanism to the culture vessel base is longer, and thus the disposition area of the adjustment passage is decreased, and the length of the passage to be retracted is longer as the distance is shorter, and thus the disposition area of the adjustment passage is increased. The disposition area of the adjustment passage is decreased on the end side of the rotational valve mechanism 903, that is, on the end side of the culture vessel base 202, so that it is possible to decrease the degradation of quality and the risks of damaging the passages caused by the contact of the passage tube of the adjustment passage with the user near the end of the culture vessel base 202 at which the user's hand and the like easily contact.

Moreover, when the description is made with reference to FIG. 15, in order to suppress the risks of entanglement of the passages, for example, as illustrated in (A) in FIG. 15, it may be fine that a cut 1501 that stably disposes the passages on the culture vessel base 202 is provided on the left and the right. It may be fine that the cut 1501 is provided one each on the left and the right, or that the cut 1501 is provided for the individual passages connected to the culture vessels 201.

Alternatively, as illustrated in (B) in FIG. 15, it may be fine that a divider 1502 is provided on the culture vessel base 202 so as to divide the passages to separate spaces for disposing the passages. As described above, the cut 1501 or the divider 1502 is provided on the passages, so that it is possible to decrease the risks of entanglement of the passages with the passage tubes connected to the other culture vessels 201.

It is noted that even in the configuration in which the passages are bundled as in the first embodiment, it may be fine that the cut 1501 is formed on the outer circumferential side of the culture vessel base 202 or on the inner circumferential side (the vacant space side) as illustrated in (C) and (D) in FIG. 15 or that a holding part that holds the passages as a divider is formed, for example.

Third Embodiment

In a third embodiment, an embodiment will be described in which the microscope is driven on the outer circumferential side of the culture vessel base for observation. In the case where the passage tubes are arranged on the inner circumferential side of the culture vessel base 202 described in the first embodiment, it is possible that the microscope is provided and driven on the outer circumferential side because the passage tubes that possibly become obstacles in driving the microscope drive do not exist on the outer circumferential side.

Figure 16:
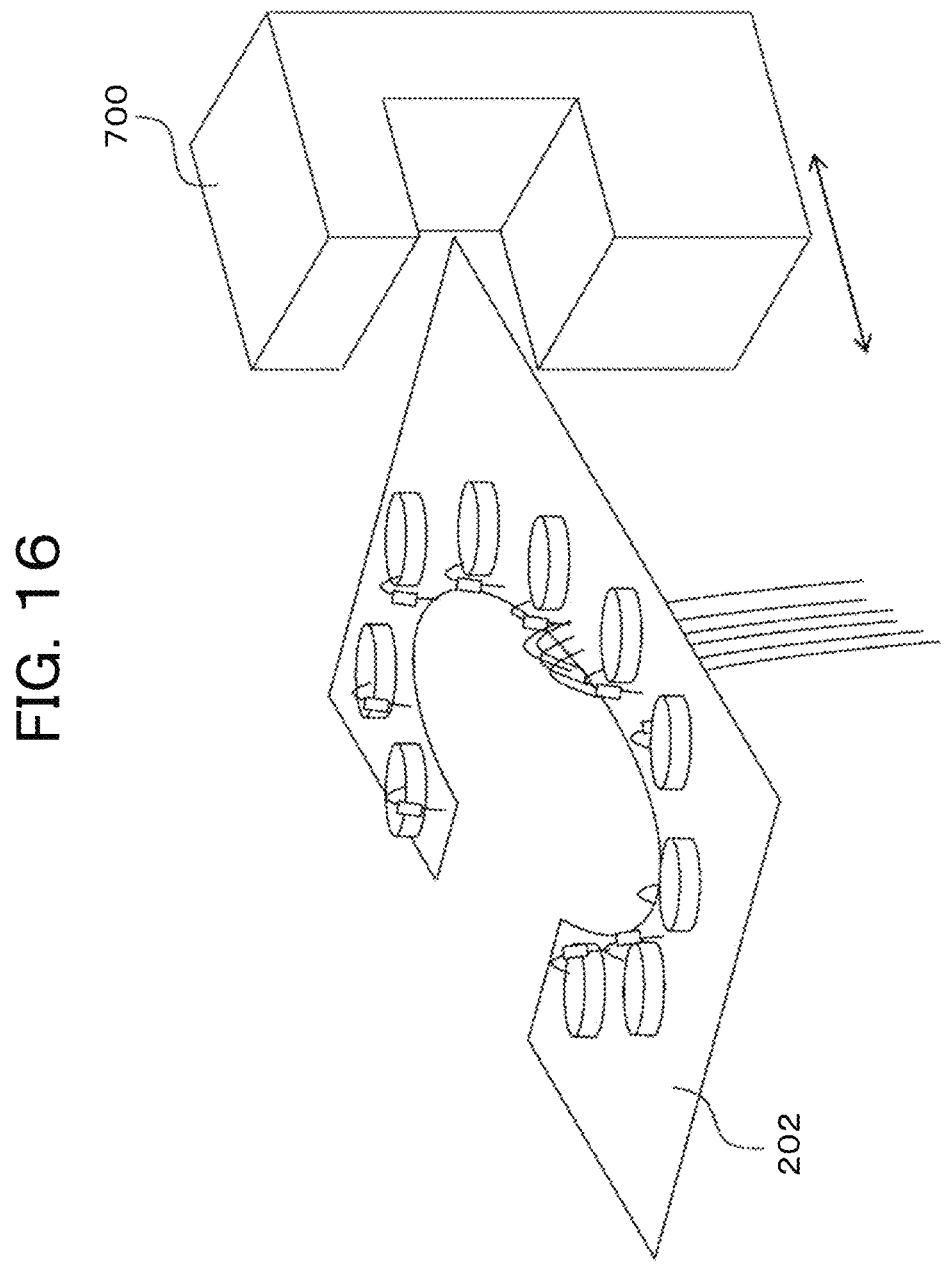
FIG. 16 is a diagram of a culture vessel base according to a third embodiment.

FIG. 16 is an example for the configuration according to the embodiment in which passage tubes are disposed toward the center part of the culture vessel base 202 and the microscope 700 is moved on the outer circumferential side of the culture vessel base 202 for observation. The volume of a bundle of the passage tubes is smaller than the volume of the microscope 700, so that the vacant space on the inner side of the culture vessel base 202 can be formed smaller than in the first embodiment, and the overall device can be downsized.

Fourth Embodiment

In the first, second, and third embodiments, the configuration is described in which the microscope is disposed on the center or the outer circumference of the culture vessel base. However, the shape of the culture vessel base and the position at which the microscope is disposed are not limited to the configuration. In the following, an embodiment will be described as a fourth embodiment in which the microscope and the culture vessel base are disposed differently from the embodiments above.

Figure 17A:
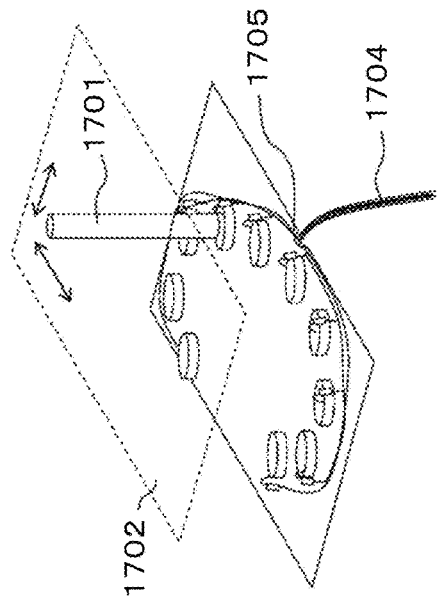
FIG. 17 is a diagram of the dispositions of a microscope according to a fourth embodiment.
Figure 17C:
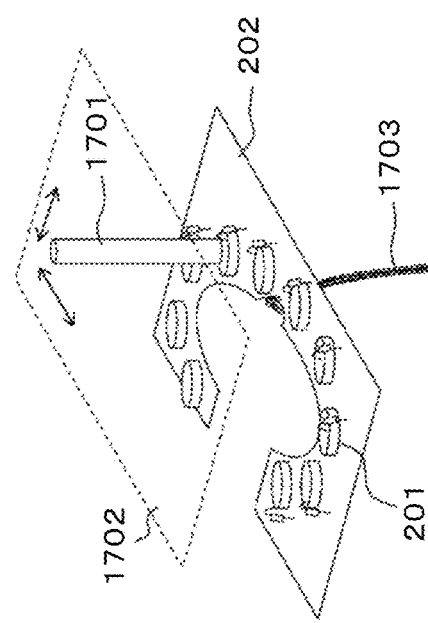
Figure 17B:
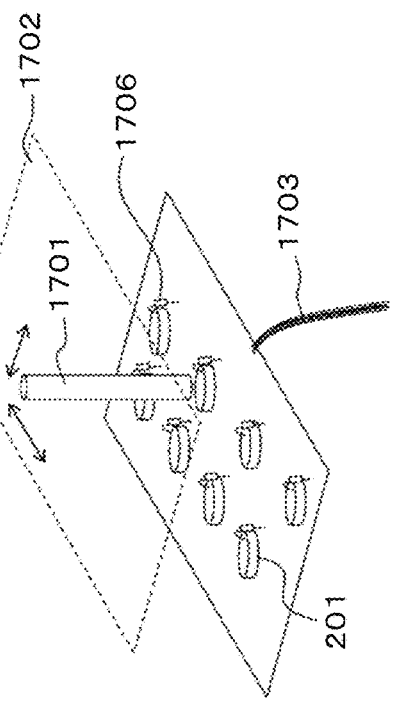

(A) in FIG. 17 is an exemplary configuration. This is a scheme in which a CCD camera microscope 1701 including a lens and a light is disposed on a top face 1702 of the incubator and the culture vessels are observed from the upper side. A rail on which the microscope 1701 operates is provided on the ceiling. With this configuration, the internal components such as the microscope, which is a factor of an obstacle in disposing the passage tubes, do not exit on the inner circumferential side of the culture vessel base 202, so that it is possible to dispose the passage tubes so as to pass on the inner circumferential side of a culture vessel base 2102. As described above, the passage tubes are disposed on the inner circumferential side of the culture vessel base, that is, on the inner circumferential side on which a plurality of the culture vessels 201 is provided, so that the lengths of the passages can be further shortened because it is unnecessary to dispose the passage tubes on the outer circumferential side. Moreover, the passage tubes are disposed in a form of convergence on the inner circumferential side, so that the passages can be bundled on the portion closer to the culture vessels. Thus, the curvature and the like of the passage tubes can be made uniform as compared with the case where the passage tubes are disposed on the outer circumferential side of the culture vessel base, so that it is possible to uniformize shear stress caused by the passage tubes, and it is possible to uniformize the quality of cells in the culture vessels 201.

Furthermore, when the passage tubes connected to the culture vessels in the center of the vacant space provided on the inner circumferential side are bundled, the distance from the culture vessels to the position at which the passage tubes are bundled (the distance of the radius of the vacant space in a circular shape) is made equal, so that it is unnecessary to provide the adjustment passage and the like, and it is possible to easily make the lengths from the branch part to the passages equal.

Moreover, in the case where the passage tubes are disposed on the outer circumference, there is a problem in that it is complicated for the user to handle the culture vessel base 202 and human errors easily occurs because the passage tubes are disposed on the side close to the door part. However, with the configuration described above, risks that the user contacts the passage tubes can be decreased, so that it is possible to suppress human errors.

(B) in FIG. 17 is an example in which a passage tube bundle 1704 is bundled and passed through a notch 1705 provided on the outer circumference on the door part side of the culture vessel base 202. This exemplary configuration also has a scheme in which the microscope 1701 that is the observation part is hung from above the device, so that it is unnecessary to provide a vacant space and the like on the culture vessel base 202, and as a result, the culture vessel base is decreased, and it is also possible to decrease the disposition area of the device. Moreover, in the case of this example, since the shape of the culture vessel base or the position at which the culture vessels are disposed does not depend on the position at which the observation part is disposed, it may be fine that the culture vessels 201 are disposed in a shape other than the circular shape on the circumference.

For example, it may be fine that as illustrated in (C) in FIG. 17, the culture vessels 201 are aligned in lines and disposed in plural lines in a parallel manner. In this example, a sterile detachable part 1706 for the individual culture vessels 201 is disposed on the same side as a passage tube bundle 1703 disposed on one side. Moreover, in the case where the passage tubes around the culture vessel base are not bundled and are disposed in a discrete manner, the distances to the passage tubes of the culture vessels can be made shorter, and it is desirable to dispose the sterile detachable part 1706 in the direction of the outer circumference.

Fifth Embodiment

An embodiment will be described as a fifth embodiment with reference to FIG. 18 in configurations of culture vessel bases in different shapes in the case where the microscope is disposed on the floor of the incubator or the side surface. It is noted that it is without saying that the shapes of the culture vessel bases described in the embodiment may be adapted to the configuration as described in the second embodiment in which the microscope is hung from the top face of the incubator.

Figure 18A:
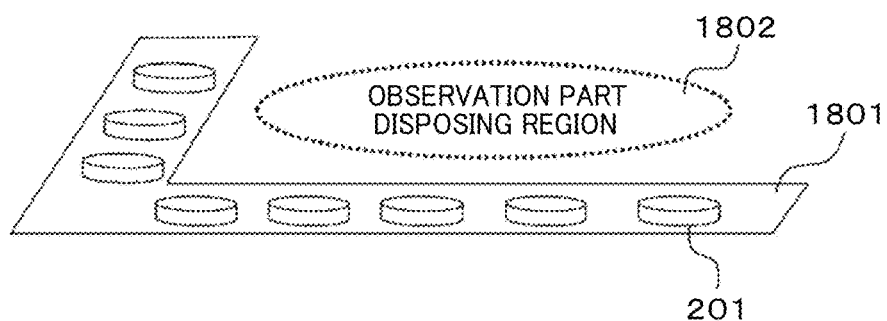
FIG. 18 is a diagram of a microscope and a culture vessel base according to a fifth embodiment.
Figure 18B:
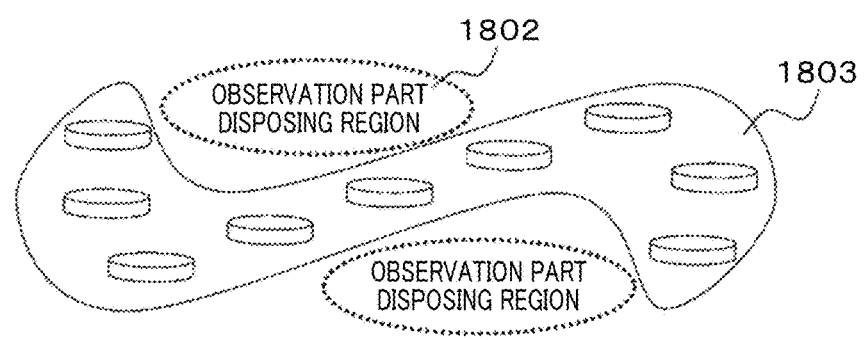
Figure 18C:
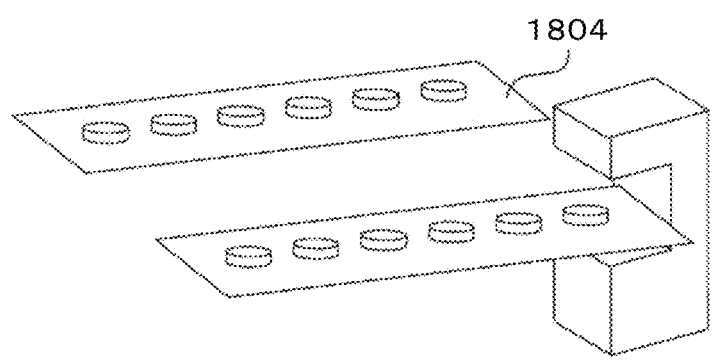

(A) in FIG. 18 is the case where the culture vessel base is bent in an L-shaped crank (in the following, the description is made the shape is referred to as "L-shape"). As illustrated in (A) in FIG. 18, with an L-shape culture vessel base 1801, the range of driving a microscope can be narrowed while securing an observation part disposing region 1802, that is, the space in which the microscope is disposed. Since the culture vessels 201 are disposed along the L-shaped culture vessel base 1801, the rotation angle of the microscope in observation is an angle of 90°. The rotation angle of the microscope is almost an angle of 360° in the U-shape disposition in the first embodiment, whereas the rotation mechanism of the microscope can be made smaller as the angle becomes small.

Moreover, as illustrated in (B) in FIG. 18, when a culture vessel base 1803 in an S-curve shape is used, the observation part disposing region 1802 that is a space for disposing the microscope can be secured at two places. In this case, two microscopes are used at the same time, and it is possible to shorten time for microscopic observation. Furthermore, the rotation angle of the microscope is an angle of 180° in observation, and the angle is almost half as compared with an angle of about 360° in a U-shape, and it is possible to downsize the rotation mechanism.

In addition, it may be fine that as illustrated in (C) in FIG. 18, the culture vessels 201 are arranged in a line, a plurality of arrangements 1804 is set in the direction of a short axis in a parallel manner, and the observation part is passed between the arrangements. Thus, the motion of the observation part to and fro is shortened, and a large number of the culture vessels 201 can be observed, so that it is possible to decrease a space for disposing the culture vessels or a space for disposing the rail to drive the observation part to and fro.

Sixth Embodiment

In the sixth embodiment, an embodiment in another configuration will be described in the case where a U-shape culture vessel base is used as illustrated in FIG. 19 as in the first embodiment. As illustrated in (A) in FIG. 17, this is the case where the culture vessels 201 are disposed in a double or greater on the same plane on the culture vessel base 202 illustrated in the first embodiment. Thus, it is possible to integrate a plurality of the culture vessels. (B) in FIG. 17 is the case where the culture vessel base 202 illustrated in the first embodiment is disposed in multiple layers. This similarly implements integration.

Moreover, in the first embodiment and the other embodiments, an example is described in which the U-shape culture vessel base is slid and the microscope is disposed on the vacant space. However, it may be fine that such a shape is formed in which a circular or a horseshoe-shaped hole part is provided on the base and the culture vessels are disposed on the culture vessel base from above the microscope through the hole part.

Seventh Embodiment

In a seventh embodiment, an embodiment will be described in which in the microscope according to the first embodiment, another imaging part is disposed around the microscope. FIG. 7B is a diagram that a phase contrast microscope is disposed on the front surface of a microscope 705 and a pH evaluation device is disposed on the back face by color temperature measurement. The pH evaluation device includes a web camera 703 and a white color board 704.

pH is determined by the color temperature of a culture medium. For example, in the case where phenol red is used for the pH indicator of the culture medium. Acid exhibits nearly yellow, and alkaline exhibits nearly red. The white color board 704 is used for the background, so that a clear image can be taken using the web camera 703. In the taken image, pH is evaluated from the quantified values of red, blue, and green components, for example. Alternatively, an absorptiometer is mounted for evaluation.

As described above, another imaging part is provided on the microscope 705, so that it is possible to efficiently evaluate cells, and it is possible to improve evaluation accuracy because of using another part. More specifically, the microscope 705 includes an operating part 702 that is a drive part as a rotation function similarly to the microscope 700 according to the embodiments described above, so that this configuration can be performed without using another microscope, and the disposing space can be made smaller as well.

Eighth Embodiment

Figure 20:
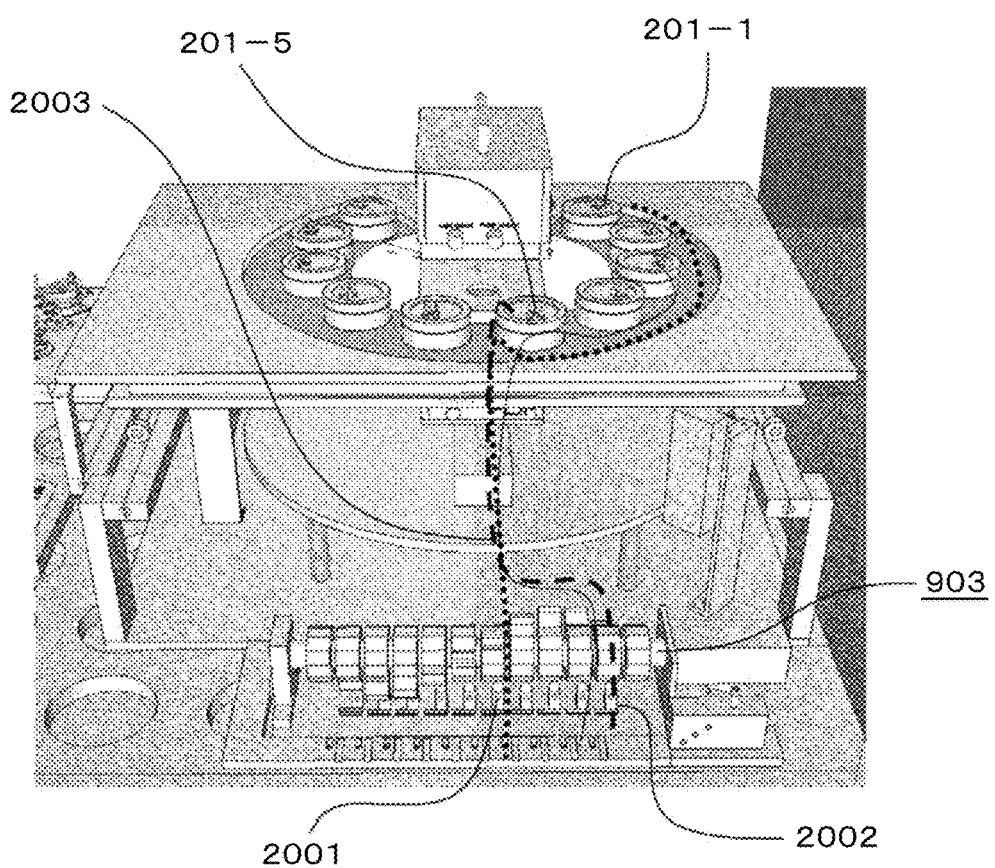
FIG. 20 is a diagram of a microscope and a culture vessel base according to an eighth embodiment.

In an eighth embodiment, as illustrated in FIG. 20, an embodiment will be described in which the lengths of the passage tubes connected to the culture vessels and the rotational valve mechanism are made more equal and shorter. As described in the first embodiment, the passage tubes are bundled on the rotational valve mechanism 903 side. Since the culture vessels 201 are disposed in a circular shape on the culture vessel base 202, the length from a point 2001 at which the passage tubes are bundled (referred to as a convergence point) to the culture vessels 201 is varied. On the other hand, as apparent from FIG. 20, since the valves (clips) that opens and closes the passage tubes at the culture vessel base 903 are lined up side by side at the rotational valve mechanism 903, the lengths of the passage tubes from the valves 2001 and 2002 to the convergence point 2003 are also varied.

Therefore, a passage tube depicted by a broken line, which is connected to the culture vessel 201-5 in a close distance from the convergence point 2003, is disposed on the valve 2002 far from the convergence point 2003, that is, disposed on the end side of the rotational valve mechanism 903, and a passage tube depicted by a dotted line connected to the culture vessel 201-1 in a long distance from the convergence point is disposed on the valve 2001 in a close distance from the convergence point 2003, that is, disposed on the center side of the rotational valve mechanism 903.

As illustrated in FIG. 20, in the embodiment, the passage tube from the culture vessel 201-1 disposed at the furthest position in the distance from the rotational valve mechanism 903 is connected to the valve 2001 in the center of the rotational valve mechanism 903, and the passage tube from the culture vessel 201-5 at the closest position in the closest distance from the rotational valve mechanism 903 to the valve 2002 located on the furthest end of the rotational valve mechanism 903, so that it is possible to dispose the passage tubes as the distances are made equal and the lengths of the passage tubes are shortened. Moreover, the redundant portion of the lengths of the passages for making the lengths equal is also small, so that it is possible to suppress the adjustment region on which the adjustment passage is disposed at the minimum.

Ninth Embodiment

Figure 21A:
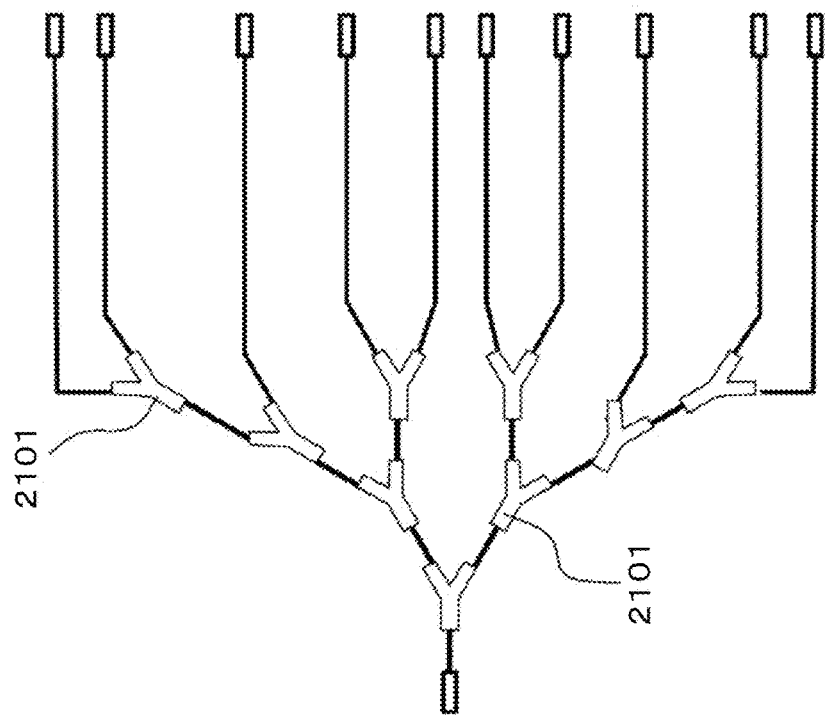
FIG. 21 is a diagram of multi-branch parts according to a ninth embodiment.
Figure 21B:
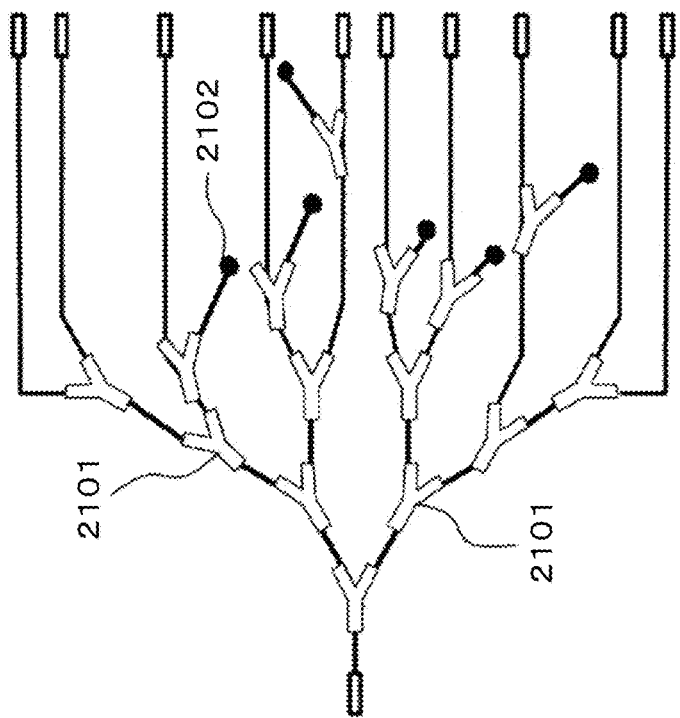

For a ninth embodiment, an embodiment will be described with reference to FIG. 21 in which the conditions of carrying cells are made uniform when cells are passed through the passage tubes. As illustrated in FIG. 21, in an automatic culture device according to in the embodiment, such a configuration is provided in which the multi-branch part at which the liquid solution is distributed from the cell bottle to the culture vessels is branched in an exponentiation of two, in turn through a two-branch part and finally ten branched passages are formed.

In the case of a configuration illustrated in (A) on the left side in FIG. 21, the number of relayed two-branch parts 2101 is different for the individual branched passages. Since the passage diameters are different at the connection point between the two-branch part 2101 and the passage tube, a step is produced. Moreover, friction applied to the liquid solution is different from friction applied to the passage tube at the two-branch part 2101. In other words, since shear stress occurs on cells every time passed through the two-branch part 2101, the conditions for cells to be cultured are different as a number of the two-branch part 2101 that relays the branched passages is varied as three or four. Thus, it is likely that the quality of cells after cultured is not uniform.

Therefore, as illustrated in (B) on the right side in FIG. 21, four two-branch parts 2101 that relay the branched passages are connected in the same number, and the conditions of carrying the liquid solution into the culture vessels 201 are made equal, so that it is possible to uniformize the quality of cells to be cultured. In the branches of the two-branch parts 2101, for the branch at which the passage tube is not connected, a closed part 2102 is formed on the route by thermal welding, for example. Moreover, it may be fine that a relay member having the same material and the same passage diameter as the two-branch part is used, not using the two-branch part that one side of the passage is closed as described above.

Tenth Embodiment

This embodiment is an embodiment in a configuration in which in the passage disposition on the device according to the first embodiment, a pressure sensor is provided on the inside of the passage and the normality of passage disposition on the device can be accurately determined.

Figure 22:
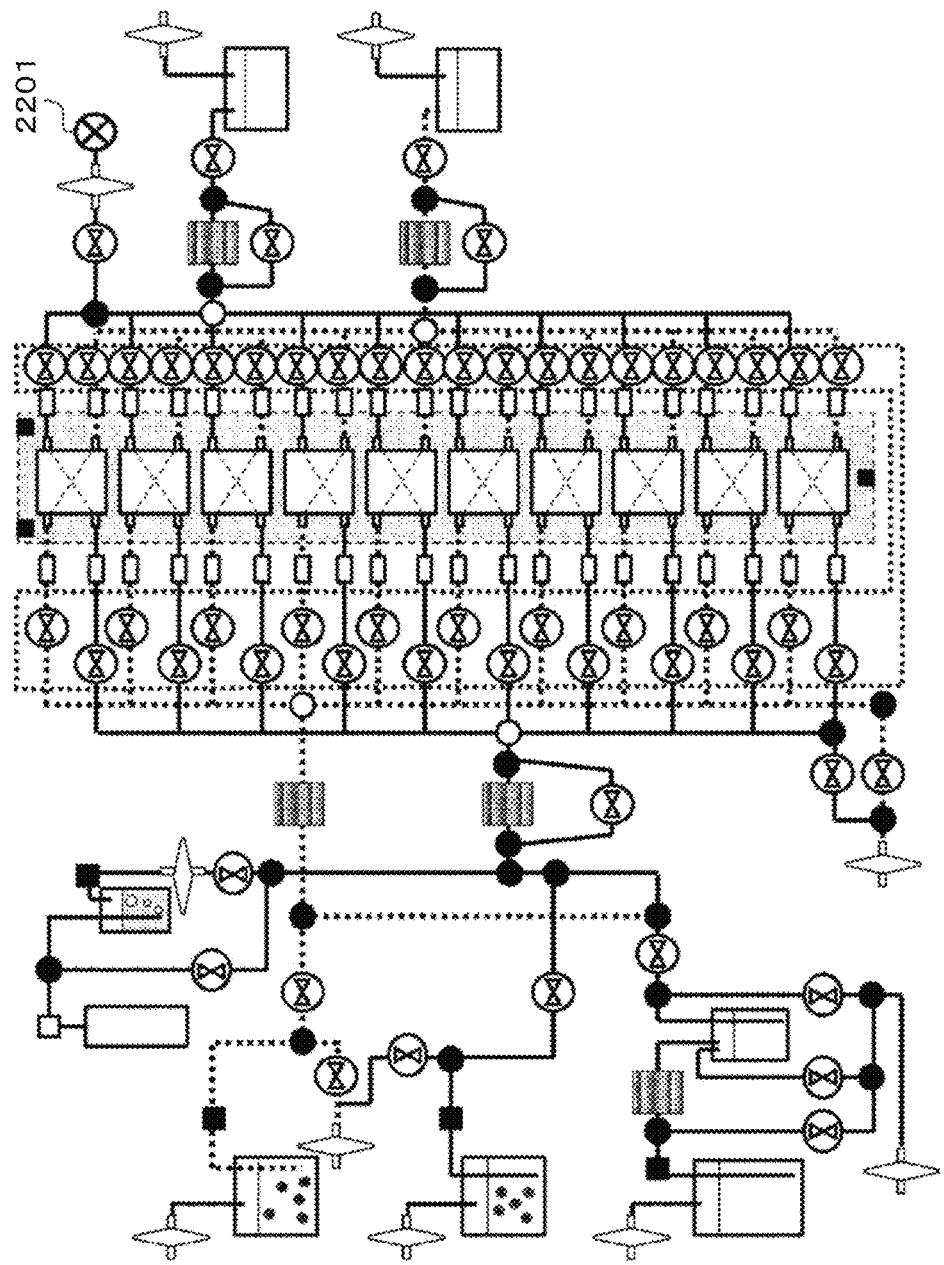
FIG. 22 is a diagram of the disposition of passages according to a tenth embodiment.

More specifically, in a passage circuit in FIG. 22, a pressure is increased and decreased in the state in which the solenoid valve provided on the rotational valve mechanism is in turn opened and closed, and the normality of passage disposition and the presence or absence of damage to the passage are evaluated in the unit of the solenoid valve. On the passage in the shortest route from the gas cylinder to the pressure sensor, the solenoid valve in the route is opened, and a gas is supplied from the gas cylinder. Thus, it is evaluated whether a pressure is increased using a pressure sensor 2201. It is noted that in FIG. 22, all the configurations are the same as the configurations in FIG. 2 except the pressure sensor 2201, and the figure numbers described in FIG. 2 are not described.

In the case where a pressure is increased, it is determined that damage to the passage is not present in the route. In the case where a pressure is decreased, the passage is replaced with a new one because damage to the passage is present. Subsequently, in the state in which a pressure is increased, one solenoid valve in the route is opened. In the case where a pressure is decreased by the opening, it is determined that the solenoid valve is normally operated. In the case where a pressure is not decreased, since the solenoid valve fails or the passage tube is not normally disposed due to some cause, the operation of this solenoid valve is confirmed, and the situations of disposing the passage tube are confirmed. Similar operations are performed to all the solenoid valves in the route in failure.

After the confirmation of the normality of passage disposition and the presence or absence of damage to the passage in the shortest route, similar confirmation is performed on the solenoid valve on the outer side of the shortest route. In other words, a gas is supplied from the gas cylinder, and it is confirmed whether a pressure is increased to the second route including the shortest route and the passage to a solenoid valve on the outer side. Subsequently, the solenoid valve is opened to confirm whether a pressure is decreased. It is possible to confirm the operation of the solenoid valve, the normality of the passage tube, and the presence or absence of damage to the passage to the solenoid valve from the processes described above. This operation is in turn performed to all the solenoid valves using signals from the control part.

With the configuration described above, it is possible to avoid errors in disposing the passages, and it is possible to implement safe automatic cultivation.

INDUSTRIAL APPLICABILITY

The present invention is useful as a culture device that uses culture vessels to culture cells or tissue by automatic manipulation, and more specifically, the present invention is useful as an automatic culture device that can manufacture regenerated tissue usable for tissue engineering.

It is noted that the present invention is not limited to the foregoing embodiments, and includes various exemplary modifications. For example, the foregoing embodiments are described in detail for better understanding of the present invention, and not necessarily limited to ones including all the configurations in the description. Moreover, a part of the configuration according to an embodiment can be replaced by the configuration of another embodiment, and the configuration of another embodiment can be additionally provided on the configuration an embodiment. Furthermore, for a part of the configuration of the embodiment, the other configurations can be additionally provided, removed, and replaced.

Furthermore, for the configurations, functions, processing parts, and the like described above, an example is described in which a program that implements a part or all of them is created. However, it is without saying that it may be fine that a part or all of them are implemented by hardware as by designing a part or all of them using an integrated circuit, for example.

LIST OF REFERENCE SIGNS 1 culture vessel part
2, 1203 passage part
3, 213, 903, 1202 rotational valve mechanism
4 cell bottle part
5 culture medium bottle part
6 preheat bottle part
7 discharge bag part 8 observation part
9 incubator part
10, 1306 gas supply part
11 humidification bottle part
12 control part
13 control terminal
201 culture vessel
202, 1201, 1204 culture vessel base
203, 504, 901, 1202 actuator
204, 205, 601 cell bottle
206 passage circuit (1)
207 passage circuit (2)
208 culture medium bottle
209, 608 preheat bottle
210 branch part
211, 401 tube pump
212, 402 solenoid valve
214, 215 discharge bag
216, 804 gas cylinder
217 air flowmeter
218, 614 humidification bottle
219 air supply circuit
220, 303, 1706 sterile detachable part
221, 606, 620 sterile connecting part
222 multi-branch part
301, 701 observation hole
302, 403, 501, 808, 2201 passage tube
404, 405, 601 cell bottle
406 preheat bottle
502 clip part
503 multiple cam part
505 spring
506 clip contacting part
602 cell bottle main body part
603 cell bottle cover part
604, 613 liquid delivery passage tube
605 internal pressure adjustment passage tube
607, 619 filter
609 receiving part
610 preheat bottle main body part
611 preheat bottle cover part
612 supply passage tube
615 humidification bottle main body part
616 humidification bottle cover part
617 air supply passage tube
618 air supply passage tube
621 connecting part
700, 705, 1201, 1309 microscope
702 operating part
703 web camera
704 white color board
801 incubator
802 door
803 surveillance monitor
805 desk
806 refrigerator
807 accommodation housing
902 passage tube
904 rotational valve mechanism stage
905 jig
1001 adjustment passage
1002 rotational valve mechanism disposition plate
1301 controller
1302 display screen
1303 incubator and others
1304 temperature adjusting part
1305 temperature sensor
1306 gas supply part
1307 liquid solution holding part and others
1308 fluid movement control mechanism part
1501 cut
1502 divider
1701, 1705 notch
1702 sill
1703, 1704 passage tube bundle
1801 L-shape culture vessel base
1802 observation part disposing region
1803 S-shape culture vessel base
2001, 2002 valve
2003 convergence point
2101 two-branch part
2102 closed part
2201 pressure sensor
2301 passage

The invention claimed is:
1. A cell culture device that cultures cells comprising:
a cabinet;
a liquid solution holding part that holds one or more liquid solutions for use in cultivation of cells; and
a plurality of passages that individually connect the liquid solution holding part to a plurality of culture vessels;
a culture vessel base that holds the plurality of culture vessels, and configured to be detachable and attachable in the cabinet; and
an observation device configured to observe an inside of the plurality of culture vessels,
wherein the passages have an equal length from the liquid solution holding part to the plurality of culture vessels,
wherein the culture vessel base defines a vacant space,
wherein the passages are disposed on an outer side of the culture vessel base, and
wherein, when the culture vessel base is attached in the cabinet, the observation device is disposed in the vacant space.
2. The cell culture device according to claim 1, wherein:
the culture vessels are connected to the liquid solution holding part through a multi-branch part to which the passages are individually connected, and
the passages have an equal length from the multi-branch part to the culture vessels.
3. The cell culture device according to claim 1,
wherein a notch that passes the observation part to the vacant space side is disposed on a part of an outer circumference of the culture vessel base.
4. The cell culture device according to claim 1, further comprising:
a supply mechanism configured to supply the one or more liquid solutions from the liquid solution holding part to the culture vessels through the passages.
5. The cell culture device according to claim 4, wherein:
the cabinet includes a door through which the culture vessel base is inserted into the cabinet,
the culture vessel base is configured to be insertable from a side of the notch into the cabinet, and
the supply mechanism is disposed on a side of the door and below the culture vessel base.
6. The cell culture device according to claim 4, wherein:
the supply mechanism includes a valve mechanism on which the passages are individually disposed,
the valve mechanism is configured to control the one or more liquid solutions to be supplied to the culture vessels, and an adjustment region is disposed on the passages between the valve mechanism and the culture vessels as a plurality of adjustment passages.

7. The cell culture device according to claim 6, wherein the adjustment region is disposed below the culture vessel base and above the supply mechanism.

8. The cell culture device according to claim 1, further comprising:
a jig that converges the plurality of passages in a bundle.

9. The cell culture device according to claim 1, wherein the passages are disposed through the vacant space.

10. The cell culture device according to claim 1, wherein a plurality of cuts are disposed on the culture vessel base and configured to hold the passages.

11. The cell culture device according to claim 1, wherein:
the observation device is configured to move in a rotation direction and in a horizontal direction, and
wherein the culture vessels are disposed around the vacant space on a circumference of the culture vessel base.

12. The cell culture device according to claim 1, further comprising:
an actuator connected to the culture vessel base and configured to change a disposition angle of the culture vessel base.

13. The cell culture device according to claim 5, wherein the door includes a flap disposed at a position higher than the culture vessel base.

14. The cell culture device according to claim 1, wherein the observation device is a microscope.

15. A cell culture device that cultures cells comprising:
a cabinet;
a liquid solution holding part that holds one or more liquid solutions for use in cultivation of cells;
a plurality of culture vessels that hold the one or more liquid solutions supplied from the liquid solution holding part;
a multi-branch part connected to the liquid solution holding part, the multi-branch part passing the one or more liquid solutions;
a plurality of passages that individually connect the multi-branch part to the plurality of the culture vessels and supply the one or more liquid solutions passed through the multi-branch part to the plurality of the culture vessels;
a culture vessel base that holds the plurality of culture vessels, and configured to be detachable and attachable in the cabinet; and
an observation device configured to observe an inside of the plurality of culture vessels,
wherein the passages have an equal length from the multi-branch part to the culture vessels,
wherein the culture vessel base defines a vacant space,
wherein the passages are disposed on an outer side of the culture vessel base, and
wherein, when the culture vessel base is attached in the cabinet, the observation device is disposed in the vacant space.

16. The cell culture device according to claim 15, wherein the observation device is a microscope.

* * * * *